(12) United States Patent
Kura et al.

(10) Patent No.: US 7,621,867 B2
(45) Date of Patent: Nov. 24, 2009

(54) INSERTION DEVICE

(75) Inventors: Yasuhito Kura, Hachioji (JP); Katsutaka Adachi, Hino (JP)

(73) Assignee: Olympus Corporation, Tokyo (JP)

( * ) Notice: Subject to any disclaimer, the term of this patent is extended or adjusted under 35 U.S.C. 154(b) by 388 days.

(21) Appl. No.: 11/599,578

(22) Filed: Nov. 14, 2006

(65) Prior Publication Data
US 2007/0066104 A1  Mar. 22, 2007

Related U.S. Application Data

(63) Continuation of application No. PCT/JP2005/008913, filed on May 16, 2006.

(30) Foreign Application Priority Data

May 14, 2004  (JP)  ............................. 2004-145703

(51) Int. Cl.
*A61B 1/00*  (2006.01)
(52) U.S. Cl. ........................... 600/137; 600/114; 439/23
(58) Field of Classification Search ................. 600/101, 600/109, 112, 114, 117, 118, 130, 132, 160, 600/172, 421–424, 137; 362/572, 574; 439/23–26
See application file for complete search history.

(56) References Cited

U.S. PATENT DOCUMENTS

| | | | |
|---|---|---|---|
| 4,374,525 A * | 2/1983 | Baba | 600/463 |
| 4,989,582 A * | 2/1991 | Sakiyama et al. | 600/109 |
| 5,022,383 A * | 6/1991 | Sakiyama et al. | 600/109 |
| 5,097,838 A * | 3/1992 | Hirooka et al. | 600/463 |
| 5,140,265 A * | 8/1992 | Sakiyama et al. | 324/220 |
| 6,577,339 B1 * | 6/2003 | Thompson et al. | 348/211.14 |
| 6,805,665 B1 * | 10/2004 | Tatsuno et al. | 600/112 |
| 2002/0045855 A1 * | 4/2002 | Frassica | 604/109 |
| 2002/0128538 A1 * | 9/2002 | Thompson | 600/121 |
| 2003/0032863 A1 * | 2/2003 | Kazakevich | 600/173 |
| 2003/0228085 A1 * | 12/2003 | Zuluaga et al. | 385/15 |
| 2004/0166464 A1 * | 8/2004 | Schneider | 433/29 |

FOREIGN PATENT DOCUMENTS

| | | |
|---|---|---|
| JP | 55-42426 | 3/1980 |
| JP | 59-181122 | 10/1984 |
| JP | 10-113396 | 5/1998 |
| JP | 2000-107123 | 4/2000 |

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An insertion device comprises a long-sized insertion portion to be inserted into a subject, a propulsion force generating portion provided on the outer peripheral face of the insertion portion, a rotating portion for rotating the propulsion force generating portion on the longitudinal axis of the insertion portion, an image capturing device for observing the image of the subject, provided at the tip of the insertion portion so as to be rotatable according to the rotation of the propulsion force generating portion, a first electric contact which is connected electrically to the image capturing device and moves rotationally according to the rotation of the propulsion force generating portion provided on the insertion portion, and a second electric contact, on which the first electric contact which moves rotationally according to the rotation of the propulsion force generating portion, is provided slidably, and is connected electrically to the first electric contact.

7 Claims, 14 Drawing Sheets

INSERTION DEVICE

CROSS REFERENCE TO RELATED APPLICATION

This application is a continuation application of PCT/JP2005/008913 filed on May 16, 2006 and claims benefit of Japanese Application No. 2004-145703 filed in Japan on May 14, 2004, the entire contents of which are incorporated herein by this reference.

BACKGROUND OF THE INVENTION

1. Field of the Invention

The present invention relates to an insertion device which is used to introduce an insertion portion of an endoscope into the body cavity to perform intracavital endoscopy, colonoscopy in particular.

2. Description of the Related Art

In recent years, an endoscope which has a flexible and slender insertion portion has been used in medical fields such as examinations or treatment. Introducing the insertion portion of the endoscope into the body cavity allows observing intracavital organs and the like without cutting, and moreover various types of remedy and treatment can be performed if necessary, by introducing treatment equipment into the body cavity through an treatment equipment insertion channel provided to the insertion portion. The endoscope has a bending portion at the tip portion of the insertion portion. The bending portion is bent in a direction either horizontal or vertical by reciprocal movement of the operation wire which is coupled with a bending piece configuring the bending portion. The operation wire can be moved back and forth by a turning operation of a bending knob provided to the operation part, for example.

With endoscopy, it is necessary to insert the insertion portion into complex body cavity portions. To insert the insertion portion into a complex lumen such as the large intestine with a 360° loop for example, an operator introduces the tip of the insertion portion toward the observation target by operating the bending knob to bend the bending portion while performing a manual operation such as a twisting operation of the insertion portion.

However, considerable skill is required to introduce the insertion portion into the deep region of the complex large intestine smoothly in a short period of time without infliction of discomfort on the patient. In other words, an inexperienced operator may delay the insertion by misdirecting the insertion portion in the deep region or may deform the course of intestines when inserting the insertion portion through to the deep region. Therefore various types proposals have been made to improve the insertability of the insertion portion.

For example, Japanese Unexamined Patent Application Publication No. 10-113396 describes a medical appliance propelling device which can guide a medical appliance up to a deep region of an organism canal easily and less invasively. This propelling device has ribs on a rotary member, the ribs being arranged obliquely as to the axial direction of the rotary member. Therefore the medical appliance coupled with the propelling device is moved toward the deep region by the propulsion force generated from the rotating movement of the rotary member because the rib converts the rotation force of the rotational member into the propulsion force.

SUMMARY OF THE INVENTION

The insertion device according to the present invention comprises a long-sized insertion portion to be inserted into a subject, a propulsion force generating portion provided on the outer peripheral face of the insertion portion, a rotating portion for rotating the propulsion force generating portion on the longitudinal axis of the insertion portion, an image capturing device for observing the image of the subject, provided at the tip of the insertion portion so as to be rotatable according to the rotation of the propulsion force generating portion, a first electric contact which is connected electrically to the image capturing device and moves rotationally according to the rotation of the propulsion force generating portion provided on the insertion portion, and a second electric contact, on which the first electric contact which moves rotationally according to the rotation of the propulsion force generating portion, is provided slidably, and is connected electrically to the first electric contact.

DESCRIPTION OF THE PREFERRED EMBODIMENTS

Hereinafter, embodiments of the present invention will be described with reference to drawings.

A first embodiment of the present invention will be described with reference to FIGS. 1 through 13.

Figure 1:
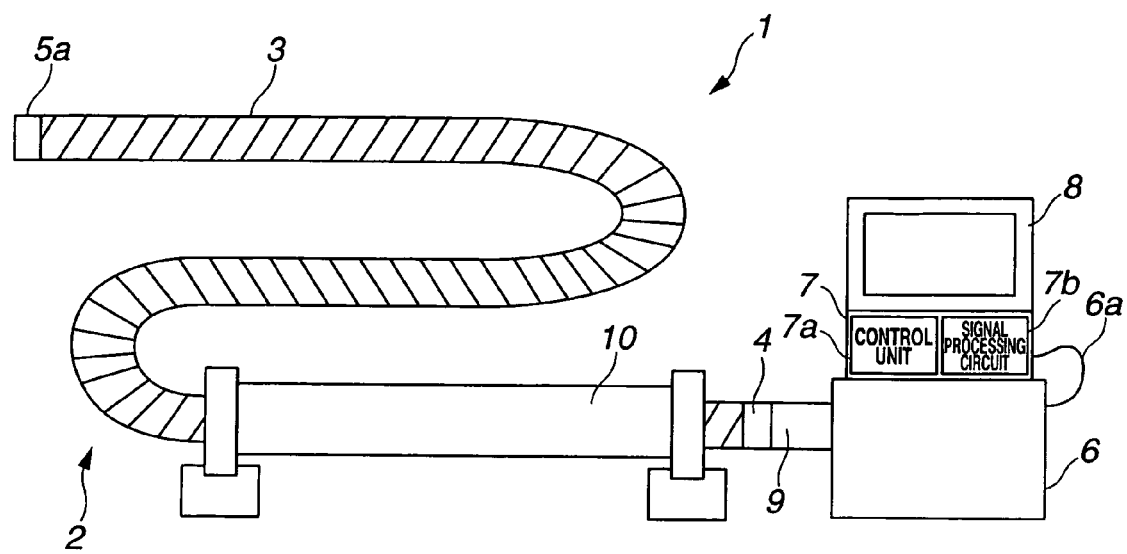
FIG. 1 is a diagram describing the configuration of the endoscope system in the first embodiment according to the present invention.

As shown in FIG. 1, an endoscope system 1 is primarily composed of an endoscopic insertion portion which is the insertion portion of the endoscope system (hereinafter, abbreviated as "insertion portion") 2, an insertion portion rotating device which is the rotating part of the endoscope system (hereinafter, abbreviated as "rotating device") 6, a video processor 7 which is the display control means, and a monitor 8 which is the display means.

The insertion portion 2 is slender and flexible. The insertion portion 2 is provided with a spiral guide tube 3. The guide tube 3 is installed for example in an integrated fashion between the connector part 4 and the endoscope tip (hereinafter, abbreviated as "tip") 5a. The connector part 4 of the insertion portion 2 is coupled with the approximate cylindrical insertion portion holding section 9 which is protruding out from the one side of the rotating device 6. The guide tube 3 is inserted through the protection pipe 10 which fits loosely. This prevents the insertion portion 2 from contacting the floor in the operating room directly.

The rotating device 6 is a device which is to rotate the insertion portion 2 in a predetermined direction on its longitudinal axis. The cable 6a connects the rotating device 6 and the video processor 7, and the cable which is not shown in the view connects the video processor 7 and the monitor 8.

The video processor 7 is provided inside with the control part 7a which controls variously and the signal processing circuit 7b which processes signals variously in its inside. The signal processing circuit 7b executes process which provides driving signals to the image capturing device 16 (see FIG. 3) which is the observation means that is placed at the tip 5a of the insertion portion 2, process which produces video signals from observation signals that are converted photoelectrically by the image capturing device 16 and are transmitted and outputs the video signals to the monitor 8, and the like, under control of the control part 7b. On the screen of the monitor 8, the endoscope image which is the image of the object that is based on the video signals which are output from video processor 7 is displayed.

Note that, as will hereinafter be described in detail, in a state wherein the insertion portion 2 is inserted to the body cavity such as the large intestine, the video processor 7 in this embodiment outputs video signals to the monitor 8, and the signals display only the still image at a predetermined rotation phase which is synchronized with the rotation period of the tip 5a of the insertion portion 2 on the screen of the monitor 8.

Figure 2:
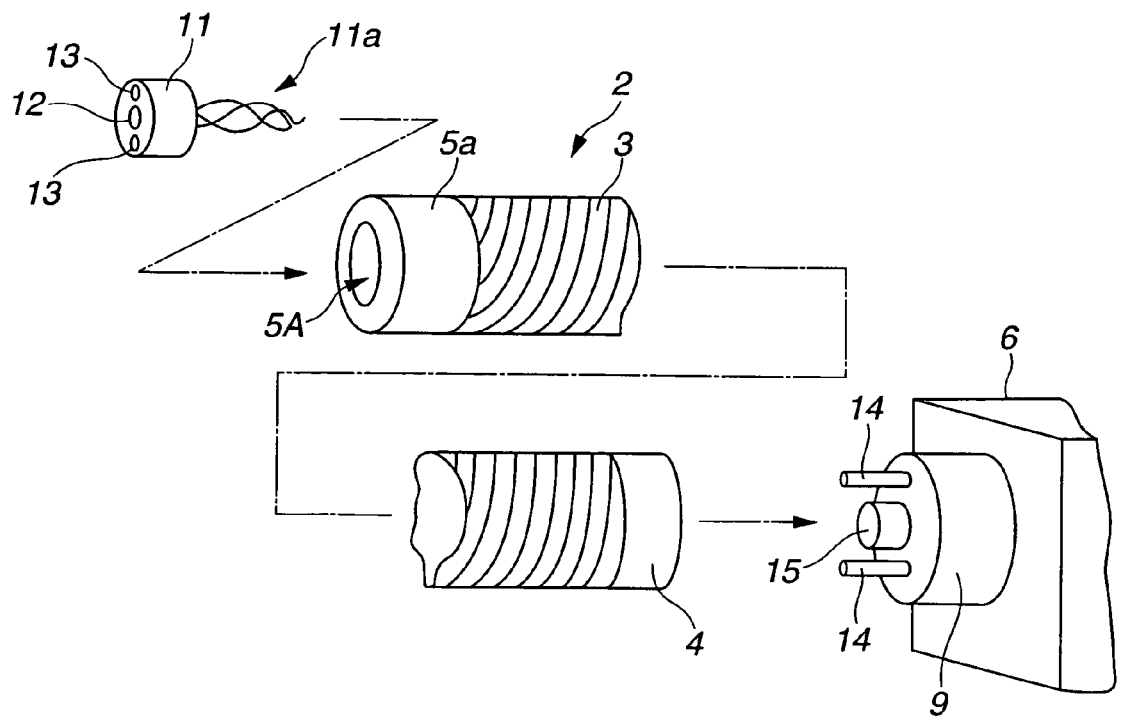
FIG. 2 is a diagram describing a connection between the insertion portion and the insertion portion rotating device.

As shown in FIG. 2, the tip 5a of the insertion portion 2 is approximately cylindrical in shape. The tip 5a is provided with an opening which contains the camera unit housing part 5A. The camera unit 11 which is the image capturing unit is housed in the camera unit housing part 5A and secured integrally and fixedly therein. The camera unit 11 is provided with an observation optical system and an illumination optical system. There is an observation window 12 at the approximate center of the distal surface of the camera unit 11. There are multiple, in this case two, illumination windows around the observation window 12. The multiple electric cables 11a are extended from the base end side of the camera unit 11. The electric cables 11a are extended through interior of the insertion portion 2 to base end part side. Note that the multiple electric cables 11a may be bundled and inserted through the interior of the insertion portion 2 as a cable bundle.

The insertion portion holding section 9 of the rotating device 6 is provided with a generally cylindrical protrusion 15 protruding from the central part of the distal surface and is provided with multiple, in this case two, pins 14 around this protrusion 15. The insertion portion 2 and the insertion portion holding section 9 are coupled and secured, mechanically and electrically, by these pins 14 and protrusion 15 fitting into the connector part 4 of the insertion portion 2.

Figure 3:
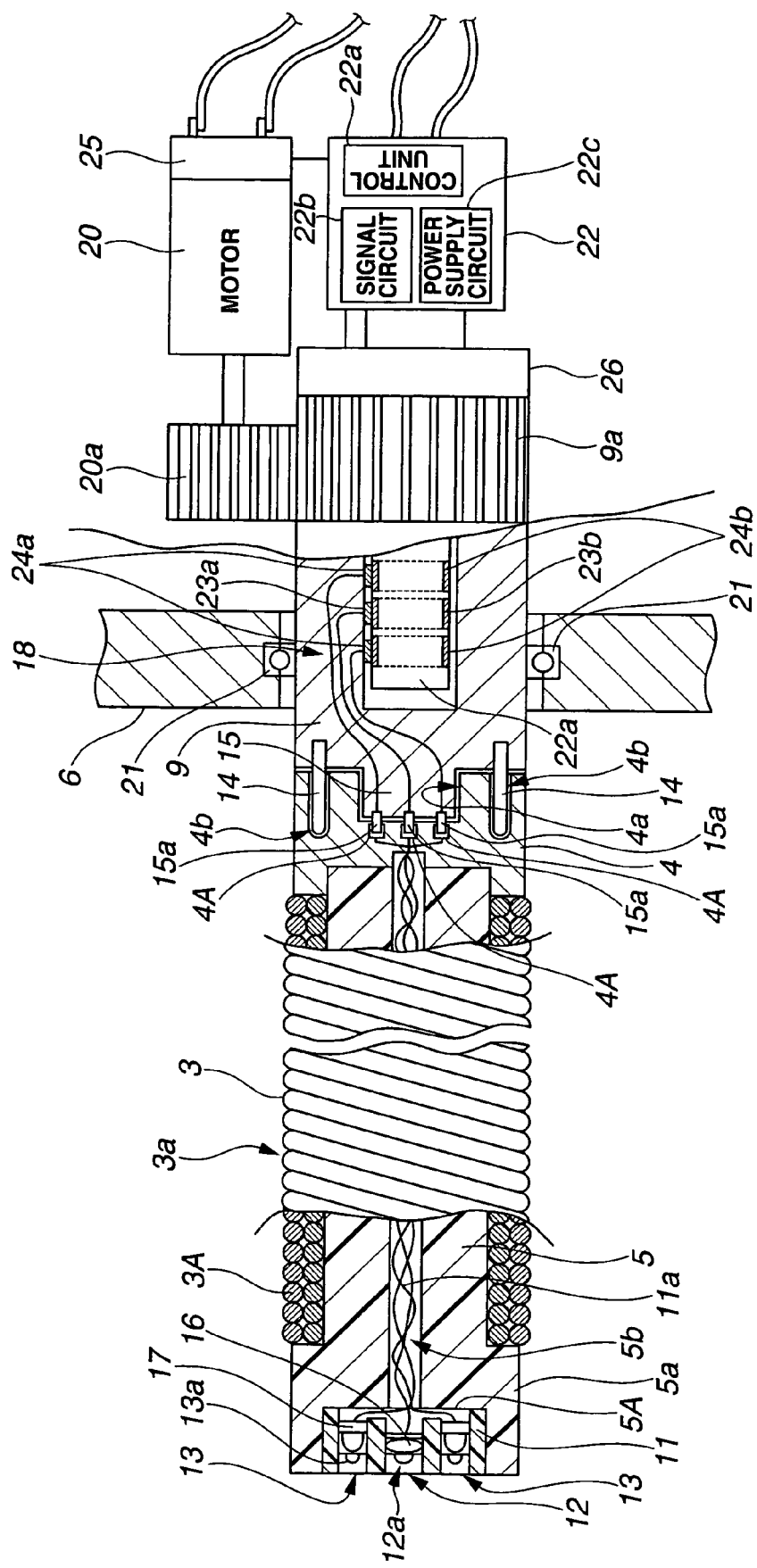
FIG. 3 is a partial cross sectional view in the longitudinal direction describing the principal members of the endoscope insertion portion.

The insertion portion 2 and the rotating device 6 are described in detail with reference to FIG. 3.

As shown in the drawing, the camera unit 11 which is secured integrally and fixedly on the tip 5a is provided with the observation optical system 12a and the two illumination optical systems 13a. The observation optical system 12a is placed toward the base end side through the observation window 12, and, for example, the image capturing device (hereinafter, referred to as "CCD") 16, serving as the observation means, is placed at base end of the observation optical system 12a. The illumination optical systems 13a are each disposed from the two illumination windows 13 toward the base side. The light-emitting diode (hereinafter, referred to as "LED") 17, which is an illumination beam irradiating part, is placed at the base end part of the illumination optical system 13a. The electric cables 11a which are extending from the base end side of the camera unit 11 are comprised of a signal transmission cable which is connected electrically to the CCD 16 and a power cable which is connected electrically to the LED 17.

Meanwhile, it is preferable that the signal transmission cable voltage and the power cable voltage are approximately the same, since this prevents various types of damage caused by the proximity of each cable, for example, damage of the CCD 16 and damage of the LED 17 caused by electromagnetic induction, and the like.

The insertion portion body 5 is formed smaller than the tip 5a in diameter. The base end part of the insertion portion body 5 extends to the connector part 4. The tip 5a is configured as a guard part to prevent the guide tube 3 from coming off. The central part of the insertion portion body 5 is provided with the through-hole 5b which the electric cables 11a that are extending from the camera unit 11 are inserted through. The insertion portion body 5 is a generally tubular member which has flexibility. The guide tube 3 is externally attached to the insertion portion body 5. The connector part 4 is fixedly secured to the base end part of the insertion portion body 5. That is to say, the guide tube 3 is placed on the outer peripheral part of the insertion portion body 5 between the tip 5a of the insertion portion 2 and the connector part 4.

The guide tube 3 is a tubular member formed by spirally winding a metal wire 3A of stainless-steel, for example, to a predetermined diameter size in a double-layered configuration, so as to have the predetermined flexibility. The guide tube 3 may be configured by winding the metal wire 3A in a spiral and multiple-wind configuration, e.g., four-wind. Various types of characteristics of the guide tube 3 can be configured by changing the degree of contact between the winds of metal wire 3A or changing the degree of spiral angle when the metal wire 3A is wound.

Therefore, the outer peripheral surface of the guide tube 3 is provided with the spiral shaped part 3a serving as the propulsion force generating portion that is formed by the surface of the metal wire 3A. The configuration of the guide tube 3 is preferably formed by winding the metal wire 3A in a left-handed spiral from the tip toward the base end. In other words, the metal wire 3A is wound spirally so that the groove of the spiral shaped part 3a of the guide tube 3 has the same direction as a thread groove of a left-hand thread. When the spiral shaped part 3a is in the rotating state at the time of insertion into the body cavity, especially into the large intestine, contact between the spiral shaped part 3a and the intestinal wall in the large intestine is improved and the insertability of the insertion portion 2 into the large intestine is improved, by forming the groove of the spiral shaped part 3a of the guide tube 3 so as to have the same direction as a thread groove of a left-hand thread.

The base end surface side of the connector part 4 is provided with a fitting hole 4a and pinhole 4b. The fitting hole 4a is a circular hole which is formed at the approximate center of the base end surface, and the protrusion 15 is placed therein. Multiple pinholes 4b, in this case two, are installed around the fitting hole 4a. The pins 14 are placed in each of the pinholes 4b. There are multiple, in this case three, contact terminals 4A on the bottom surface of the fitting hole 4a. The signal transmission cable and the power cable which are the electric cables 11a are connected to each of these contact terminals 4A.

Also, the distal surface of the protrusion 15 of the insertion portion holding section 9 is provided with three contact pins 15a which correspond to the contact terminals 4A. Therefore, when the connector part 4 and the insertion portion holding section 9 are coupled with each other, the three contact terminals 4A which are installed on the connector part 4 and the three contact pins 15a which are installed on the insertion portion holding section 9 come into contact with each other electrically. This connects the CCD 16 and LED 17 to the rotating device 6 electrically.

The insertion portion holding section 9 is held rotatably in a direction on its longitudinal axis by a bearing 21, for example, placed on the side panel of the rotating device 6. Gear grooves 9a in the shape of a spur gear, for example, are formed on the outer periphery of the base end part of the insertion portion holding section 9. A cylindrical gear 20a which is installed on the distal part of the motor shaft of the motor 20 meshes with the gear grooves 9a. Therefore, driving the motor 20 rotates the cylindrical gear 20a which is provided to the motor shaft. The insertion portion holding section 9 then is rotated in a predetermined direction, in this case counter-clockwise, from the base end toward the tip on its longitudinal axis, due to the gear grooves 9a meshing with the cylindrical gear 20a.

The rotating device 6 is provided with a collector (hereinafter, referred to as "slip ring") 18 which electrically connects the insertion portion holding section 9 that is rotated and the control device 22. The control device 22 serves as display control means, provided with a control unit 22a, a signal circuit 22b, a power supply circuit 22c, and the like. The slip ring 18 is provided with a brush part 23a which is a first electric contact, brush parts 24a which are third electric contacts, ring part 23b which is a second electric contact, and ring parts 24b which are fourth electric contacts. The brush part 23a and 24a contact the ring part 23b electrically in a slidable state. The brush part 23a and 24a are integrally installed on the predetermined part of the insertion portion holding section 9. The ring part 23b and 24b are annularly installed on the predetermined positions on the outer peripheral surface of the shaft body 22a which is extended from the control device 22. The shaft body 22a has the same central axis as the rotational axis of the insertion portion holding section 9. The signal transmission cable is connected to the brush part 23a which is the first electric contact, and the ring part 23b which is the second electric contact is electrically connected to the signal circuit 22b. On the other hand, the power cables are connected to the brush parts 24a which are the third electric contacts, and the ring parts 24b which are the fourth electric contacts are connected to the power supply circuit 22c electrically.

Moreover, the rotating device 6 is provided with a motor encoder 25 which is the rotating part detection means that detects the rotation angle of the motor 20 and with the holding part encoder 26 which is the propulsion force generating portion detection means that detects the rotation angle of the insertion portion holding section 9 which rotates the insertion portion 2 which is provided with the guide tube 3. The detection signals which are output from the encoders 25 and 26 are input into the control unit 22a of the control device 22. Note that in this embodiment, a holding part encoder 26 is provided, which outputs a detection signal each time a reference point which is set on the insertion portion holding section 9 passes a predetermined phase position. This means that a detection signal is output to the control unit 22a each time the insertion portion holding section 9 rotates 360 degrees.

The operation of the endoscope system 1 in this embodiment, which is composed as described above, will now be described.

The preparatory procedures for inserting the insertion portion 2 into the large intestine will be described.

To insert the insertion portion 2 through the large intestine, for example, to the cecum region, first of all, a doctor or nurse (hereinafter, referred to as "staff") inserts insertion portion 2 through inside of the protection pipe 10. Then, the staff couples the connector part 4 of the insertion portion 2 which protrudes from one end of the protection pipe 10 with the insertion portion holding section 9 of the rotating device 6. At this time, the staff fits each of the two pins 14 of the insertion portion holding section 9 into each of the two pinholes 4b of the connector part 4 and, holding this status, fits the protrusion 15 of the insertion portion holding section 9 into the fitting hole 4a of the connector part 4. This completes the preparations for inserting insertion portion 2 into the large intestine. Moreover, the video processor 7 and the monitor 8 are prepared along with the preparation of insertion portion 2.

Next, the procedures for inserting the insertion portion 2 into the large intestine of a patient will be described with reference to FIG. 4.

First, the staff grasps the tip of the insertion portion 2 and inserts the tip 5a of the insertion portion 2 through the anus 71 (see FIG. 4) of the patient, who is lying on a bed or the like, into the large intestine. Then, the spiral shaped part 3a of the guide tube 3 which is installed on the insertion portion 2 contacts the intestinal wall of the patient. At this time, the contact state between the spiral shaped part 3a of the guide tube 3 and the plica of the intestinal wall is like the relationship between a male thread and a female thread.

In this contact state, the staff drives the motor 20 of the rotating device 6 clockwise on the axis of insertion portion 2. Then, the insertion portion holding section 9 is rotated counter-clockwise on its axis. This rotates the connector part 4 of the insertion portion 2 which is attached to the insertion portion holding section 9 counter-clockwise to the inserting direction on its axis. As this rotation is transmitted from the base end to the tip portion of the insertion portion 2, The spiral shaped part 3a of the guide tube 3 which is installed integrally rotates counter-clockwise on its axis so as to move from the tip portion to the base end side. At this time, the camera unit 11 which is integrally and fixedly secured on the tip 5a of the insertion portion 2 rotates with the rotation of the insertion portion 2.

Then, by the insertion portion 2 being rotated, at the contact part between the spiral shaped part 3a which is rotating and the plica of the intestinal wall, propulsion force which makes the insertion portion 2 advance is generated as an external thread moves relative to an internal thread. This results in the insertion portion 2 advancing inside of the large intestine toward deep region by the propulsion force. At this time, the operator may manually operate so as to push ahead the insertion portion 2 which the staff is grasping.

Figure 4:
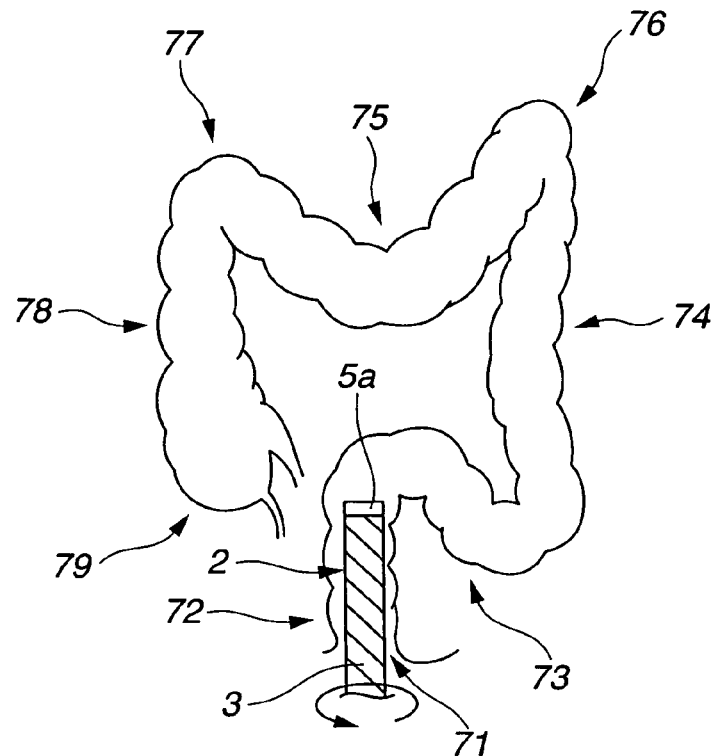
FIG. 4 is a diagram describing the insertion portion which is inserted into a large intestine.
Figure 5:
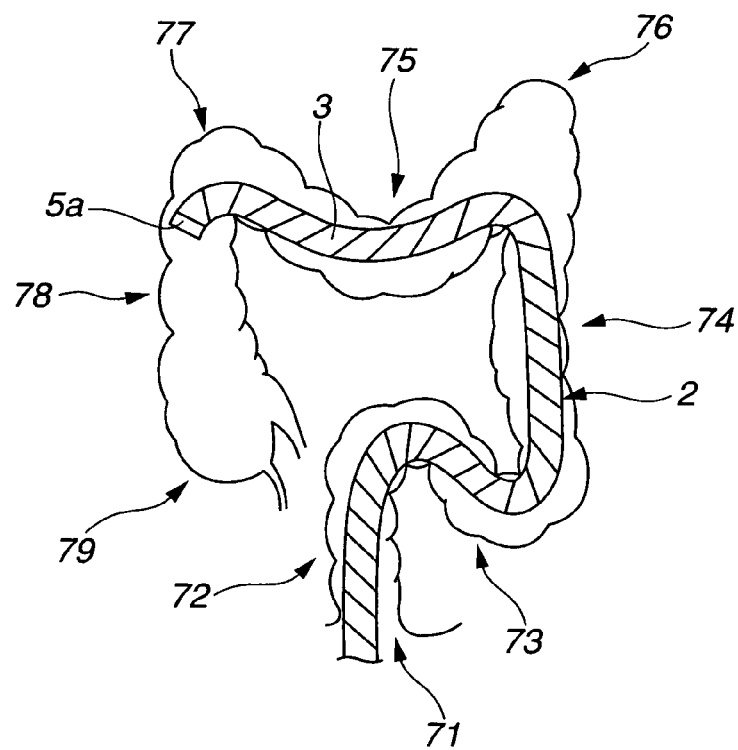
FIG. 5 is a diagram describing the insertion portion which is inserted up to a deep region of a large intestine.

As shown in FIG. 4, the rotating insertion portion 2 which is inserted through the anus 71 advances from the rectum 72 toward the sigmoid colon region 73 by the propulsion force which is generated by the guide tube 3 and the manual operation of the operator. Then, the tip 5a of the insertion portion 2 arrives at the sigmoid colon region 73. At this time, the insertion portion 2 can obtain stable propulsion force while being bent in a complex manner due to the contact between the spiral shaped part 3a of the insertion portion and the intestinal wall. In addition, because the insertion portion 2 has the predetermined flexibility, the insertion portion 2 advances along the intestinal wall smoothly without being prevented from advancing at the sigmoid colon region 73 which changes the position easily. Note that there are cases wherein the insertion portion 2 advances smoothly while forming the sigmoid colon region 73 into an alpha loop shape along the intestinal wall, when the insertion portion 2 passes the sigmoid colon region 73.

The rotating insertion portion 2 passes the sigmoid colon region 73. Subsequently, the insertion portion 2 advances smoothly along the wall of the bending region which is the border between the sigmoid colon region 73 and the descending colon region 74 which has low mobility, the splenic flexure region 76 which is the border between the descending colon region 74 and the transverse colon region 75 which has high mobility, and the hepatic flexure region 77 which is the border between the transverse colon 75 and the ascending colon 78. This makes the insertion portion arrive at, for example, neighborhood of the cecum region 79 which is the target region, without changing the course of the large intestine as shown in the FIG. 5.

While the rotating insertion portion 2 is inserted into the large intestine of the patient, the staff inserts the insertion portion 2 into the deep region of the large intestine by the propulsion force and manual operation, while confirming the endoscope image in the large intestine which is displayed on the screen of the monitor 8. At this time, in order to prevent the image which is displayed on the screen of the monitor 8 from being displayed rotationally due to the rotations of the insertion portion 2, the video processor 7 outputs to the monitor 8 predetermined video signals which prevent the endoscope image which is displayed on the screen of the monitor 8 from rotating. The video signals output from the video processor 7 to the monitor 8 are observation signals output from the CCD 16 at a predetermined phase position taking into consideration the rotation cycle of the insertion portion 2.

Here, the image capturing screen which is displayed on the screen of the monitor 8 will be described with reference to FIGS. 6 through 9.

Figure 6:
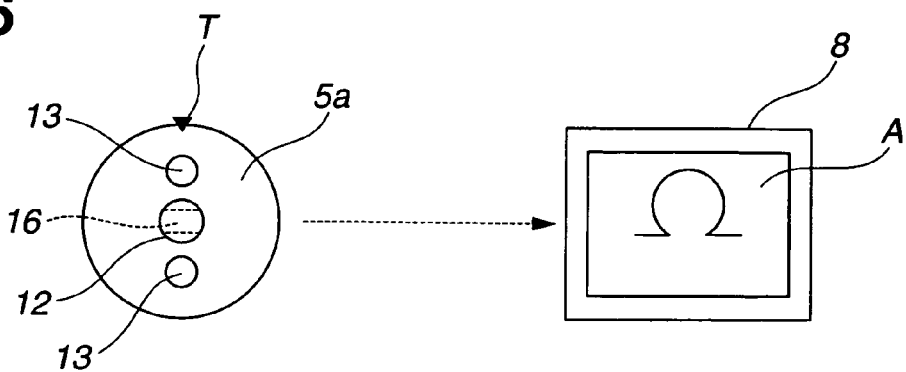
FIG. 6 is a diagram illustrating an image captured by an image capturing device provided to the insertion portion being displayed as an image A on the screen of the monitor when the insertion portion is at a predetermined phase position.

As shown in FIG. 6, the video processor 7 outputs the video signals to the monitor 8, for example, at the predetermined phase position where the triangle mark T of the tip 5a is positioned at the top portion in the drawing, i.e., at the position where the vertical position of the image of the subject image-captured by the CCD 16 and the vertical relation of the endoscope image displayed on the screen of the monitor 8, agree. Accordingly, the endoscope image image-captured by the CCD 16 positioned at the predetermined phase position shown in FIG. 6 is displayed as an image A on the screen of the monitor 8.

Figure 7:
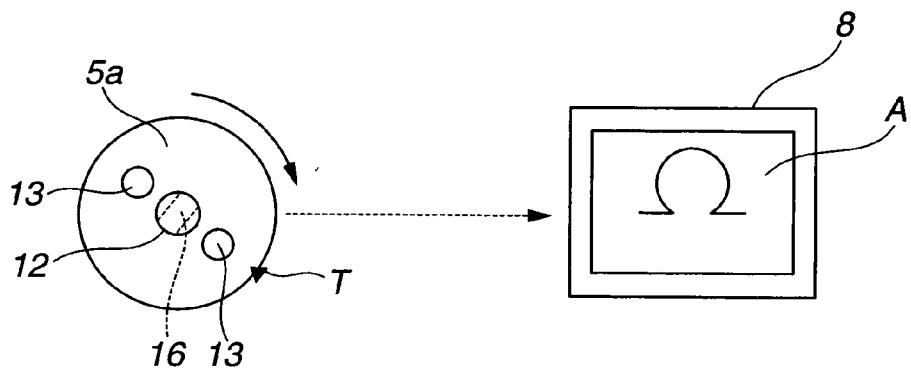
FIG. 7 is a diagram illustrating the image A being displayed on the screen of the monitor when the insertion portion is rotated from the position shown in FIG. 6.

In the state in which the position of the triangle T of the tip 5a is rotationally moved in the direction of the arrow from the position shown in FIG. 6 by 120 degrees for example, as shown in FIG. 7, i.e., the tip 5a is rotated to the predetermined phase position, the video processor 7 outputs video signals in the state that the tip 5a is positioned at the predetermined phase position to the monitor 8. That is to say, the image A same as that shown in FIG. 6 continues to be displayed on the monitor 8 screen.

Figure 8:
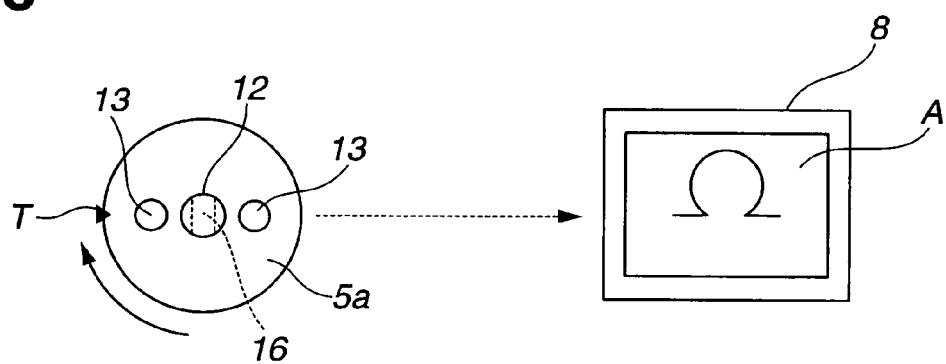
FIG. 8 is a diagram illustrating the image A being displayed on the screen of the monitor when the insertion portion is further rotated from the position in FIG. 7.
Figure 9:
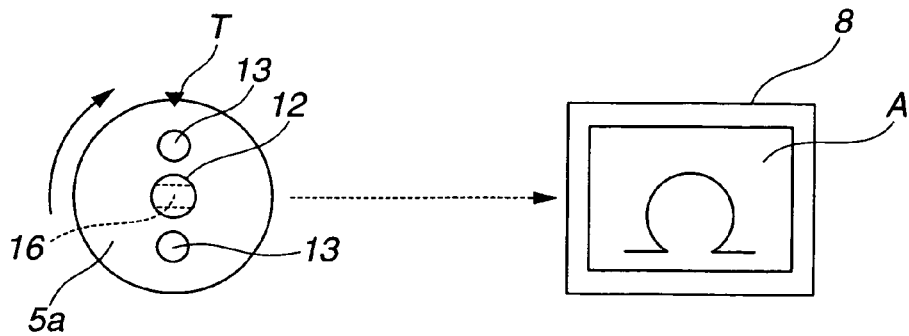
FIG. 9 is a diagram illustrating an image captured by the image capturing device provided to the insertion portion being displayed as an image B on the screen of the monitor when the insertion portion is rotated back to the predetermined phase position once again.

Also, in a state wherein the position of the triangle T of the tip 5a is rotationally moved in the direction of the arrow from the position shown in FIG. 7 by 150 degrees for example, as shown in FIG. 8, i.e., the tip 5a is rotated to the predetermined phase position, the video processor 7 outputs video signals in the state that the tip 5a is positioned at the predetermined phase position to the monitor 8. That is to say, the image A same as that shown in FIG. 6 continues to be displayed on the monitor 8 screen.

In the event that the position of the triangle T of the tip 5a returns to the predetermined phase position again, the video processor 7 outputs the video signals image-captured by the CCD 16 repositioned at the predetermined phase position to the monitor 8 anew. Thus, an image B with the same vertical relation of the CCD 16, which is different from the endoscope image image-captured by the CCD 16 at the predetermined phase position shown in FIG. 6, is displayed on the monitor 8.

That is to say, endoscope images image-captured by the CCD disposed at the predetermined phase position are sequentially displayed on the monitor 8 screen, synchronously with the cycle of one rotation of the tip 5a of the insertion portion 2.

Description will be made regarding the rotational angle information of the insertion portion holding section 9, which the rotating device 6 supplies to the video processor 7, with reference to FIG. 10 and FIG. 11.

Figure 10:
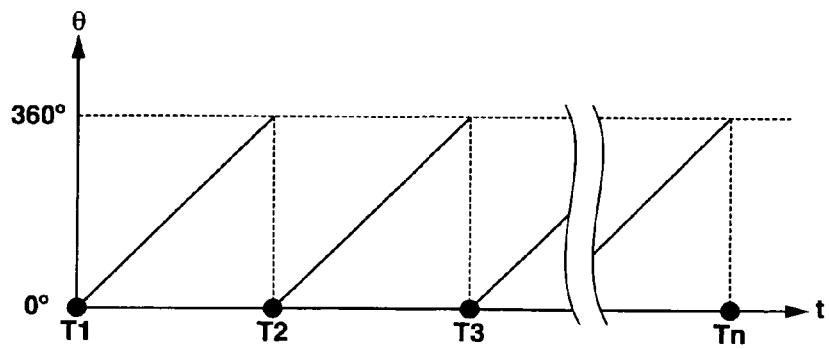
FIG. 10 is a diagram showing the relationship between the rotation angle θ of the insertion portion holding section in the insertion portion rotating device and the time t.

The control unit 22 of the rotating device 6 obtains the rotational cycle (time) t information of the insertion portion holding section 9 which rotates as shown in FIG. 10, at the rotation angle θ (0° through 360°), and information of the rotation angle θ, via the encoder 26. Specifically, upon the control unit 22a of the control device 22 which is provided to the rotating device 6 receiving a detection signal from the encoder 26, observation signals output from the CCD 16 of the camera unit 11 with a rotational angle θ of 0° is supplied to the video processor 7, under control of the control unit 22a. Now, under the control of the control unit 7a, the video processor 7 modulates the observation signals transmitted form the CCD 16 of the camera unit 11 into video signals and outputs to the monitor 8, so as to display an endoscope image on the screen of the monitor 8.

In detail, first, the control device 22 of the rotating device 6 supplies observation signals output from the CCD 16 of the camera unit 11 at the time T1 where the insertion portion holding section 9 shown in FIG. 10 is at the rotation angle of 0°, to the video processor 7. Here, the video processor 7 generates video signals at the rotation angle 0° and time T1 and outputs to the monitor 8. Accordingly, an endoscope image V1 is displayed on the screen of the monitor 8 as shown in FIG. 11. Subsequently, the video processor 7 consecutively outputs video signals for displaying the endoscope image V1 shown in FIG. 11 on the monitor 8, while the insertion portion holding section 9 of the rotating device 6 is rotating from the time T1 to the time T2, i.e., while the rotation angle θ of the insertion portion holding section 9 moves between 0°<θ<360°.

Figure 11:
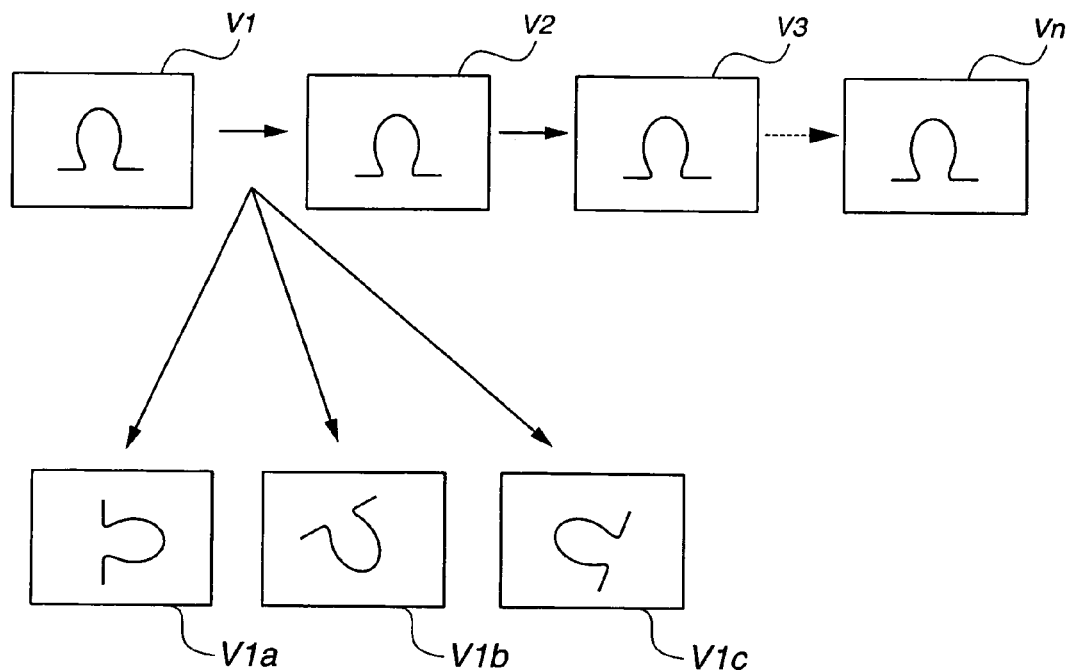
FIG. 11 is a diagram describing the relationship between the image which corresponds to the rotation angle θ of the insertion portion holding section in the insertion portion rotating device and the time t in FIG. 10 and the image which is displayed on the screen of the monitor.

That is to say, when the time t shown in FIG. 10 is T1 ≦t≦T2, only the endoscope image V1 shown in FIG. 11 is consecutively displayed on the screen of the monitor 8. Accordingly, when the rotational angle θ of the insertion portion holding section 9 of the rotating device 6 is between 0°<θ<360°, the observation signals output from the CCD 16 of the camera unit 11, i.e., observation signals corresponding to the endoscope image V1a at the rotation angle θ of 90°, observation signals corresponding to the endoscope image V1b at the rotation angle θ of 150°, and observation signals corresponding to the endoscope image V1c at the rotation angle θ of 300°, are all not generated into video signals.

Next, the control device 22 of the rotating device 6 supplies the observation signals output from the CCD 16 of the camera unit 11 at the time T2 where the rotational angle of the insertion portion holding section 9 shown in FIG. 10 is 0° to the video processor 7. Accordingly, an endoscope image V2 shown in FIG. 11, at the rotational angle 0° and time T2 that has been generated at the video processor 7, is displayed on the monitor 8 screen. The endoscope image V2 is consecutively displayed on the screen of the monitor 8 during the time t of T2 ≦t ≦T3.

Next, the rotating device 6 supplies predetermined observation signals to the video processor 7 at the time T3 where the rotation angle of the insertion portion holding section 9 shown in FIG. 10 is 0°. Accordingly, an endoscope image V3 shown in FIG. 11, at the rotational angle 0° and time T3 that has been generated at the video processor 7, is displayed on the monitor 8 screen.

The video processor 7 continues to output an endoscope image Vn shown in FIG. 11 at the point in time of Tn shown in FIG. 10 where the rotational angle θ of the insertion portion holding section 9 is θ=0°, i.e., the predetermined phase position, based on the information of the rotational cycle (time) t of the insertion portion holding section 9 supplied from the control device 22 of the rotating device 6, and information of the rotational angle θ, until the rotational angle θ of the insertion portion holding section 9 is the next θ=0°. Accordingly, the endoscope image Vn is consecutively displayed on the monitor 8 screen until the rotational angle θ of the insertion portion holding section 9 is the next θ=0°.

Note that an arrangement may be made wherein, at the time of displaying the endoscope image on the monitor 8, rotational correction processing is performed by the video processor 7 so as to display the image as a normal video on the monitor 8 in accordance with the rotational cycle of the rotating device 6. Accordingly, the video displayed on the monitor 8 screen is displayed as a normal observation image without being rotated. In this rotation correction processing, the observation window 12 is disposed at the approximate middle of the camera unit 11. Accordingly, the optical axis of the observation window 12 is on the rotational axis of the insertion portion 2.

The staff inserts the insertion portion 2 to the deep portion of the large intestine while checking the endoscope image displayed on the monitor 8 screen. At this time, manual operations are made for changing the rotation speed of the rotating device 6, and advancing the insertion portion 2 according to various bent states of the large intestine. Subsequently, the staff stops driving of the rotating device 6 upon having made a determination from the endoscope image displayed on the monitor 8 screen that the tip 5a of the insertion portion 5a has reached near the cecum region 79. Transition is then made to retract the insertion portion 2 in order to perform endoscope inspection of the large intestine. Note that an arrangement may be made for performing endoscope inspection of the large intestine wherein the staff drives to rotate the rotating device 6 in the clockwise direction on the axis from the base end toward the distal end, thereby performing retracting operation of the insertion portion 2.

Thus, with the endoscope system of a configuration wherein the guide tube provided integrally with the insertion portion is rotated by a rotating device, a spiral-shaped portion is provided on the outer face of the guiding tube. Accordingly, in the state wherein the insertion portion is inserted into the large intestine for example, the contact state between the spiral-shaped portion of the guide tube and the intestine wall is in the relation between a so-called male screw and female screw. In this contact state, the insertion portion holding section is rotated counter-clockwise on its axis by the motor of the rotating device, so as to rotate the endoscope insertion portion in the counter-clockwise direction on its axis. Thus, the rotational force is converted into propulsion force, and the endoscope insertion portion can be advanced toward the deep portions of the large intestine as a male screw moving into a female screw.

Also, according to the present embodiment, the staff can insert the insertion portion 2 toward the target portion of a deep portion in the body cavity by rotating the insertion portion 2 in the counter-clockwise direction on its axis to gain propulsion force, and while checking the endoscope image within the large intestine on the monitor 8 screen. Accordingly, the staff can easily check the bending state within the large intestine, the insertion state of the insertion portion, and so forth. Accordingly, insertion of the endoscope insertion portion to the deep portion of the body cavity can be smoothly and speedily performed, thereby reducing the load on the staff and the load on the patient.

As a result of the above, with the endoscope system 1 according to the present embodiment, at the time of inserting the insertion portion 2 into a body cavity such as the large intestine, in addition to the propulsion force obtained by the guide tube, the operator can insert the insertion portion into the body cavity such as the large intestine while observing the body cavity such as the large intestine, and therefore insertability of the insertion portion 2 to the body cavity is improved.

Note that although with the present embodiment, the body cavity to which the insertion portion 2 is to be inserted is described as being the large intestine, the body cavity where the insertion portion 2 is inserted is not restricted to the large intestine, and may be the body cavity from the oral cavity through the esophagus, stomach, and small intestine, and so forth.

Figure 12:
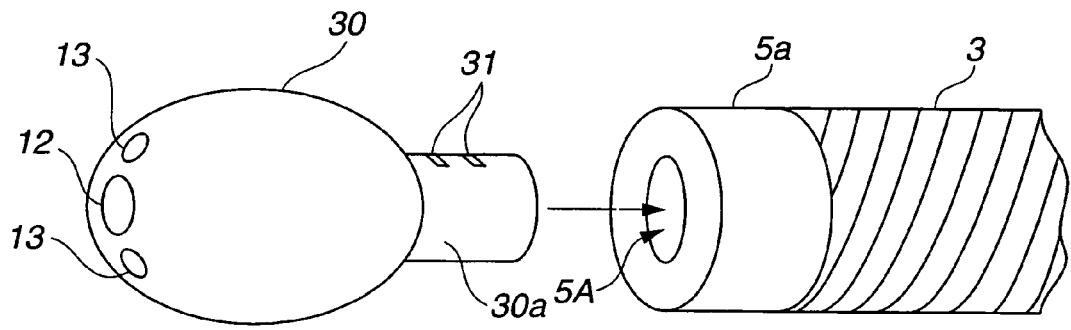
FIG. 12 is a diagram describing a camera unit which is detachably placed in the camera unit housing part provided to the tip of the insertion portion.

Also, note that a camera unit 30 may be detachably provided to the tip 5*a* of the insertion portion 2, as shown in FIG. 12. In this diagram, the camera unit 30 is fit into a camera unit storage portion 5A provided to the tip 5*a*. Note that configurations which are the same as those of the insertion portion 2 in the above-described embodiment will be denoted with the same reference numerals and description thereof will be omitted.

The camera unit 30 is formed with a smooth and generally spherical shape for the outer face, giving consideration to insertability of the insertion portion 2. Provided on the tip portion of the camera unit 30 are an observation window 12, and multiple, i.e., two illumination windows 13. The optical axis of the observation window 12 and the rotating axis of the insertion portion 2 generally agree. The two illumination portions 13 are provided around the observation window 12. A generally-cylindrical connector portion 30*a* is provided at the base side of the camera unit 30. Multiple, two in this case, contact terminals 31 are provided on the side circumferential face of the connector portion 30*a*.

Figure 13:
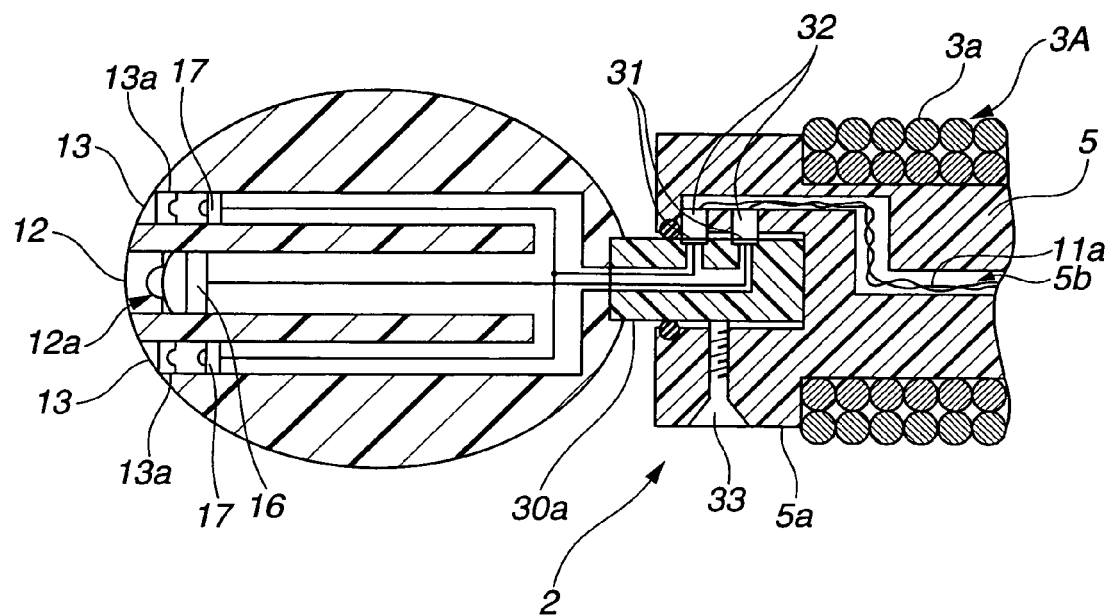
FIG. 13 is a longitudinal cross sectional view describing the configuration of the camera unit and the tip of the insertion portion.

As shown in FIG. 13, the connector portion 30*a* of the camera unit 30 is inserted into the camera unit storage portion 5A of the tip 5*a*. The connector portion 30*a* of the camera unit 30 is integrally fixed to the tip 5*a* with a fixing member 33 such as a screw or the like, to prevent from falling out from the camera unit storage portion 5A. Accordingly, as with the above embodiment, upon the insertion portion 2 entering a rotating state, the camera unit 30 integrally fixed to the tip 5*a* also rotates with the rotations of the insertion portion 2.

An observation optical system 12*a* is disposed from the observation window 12 of the camera unit 30 toward the base side. The CCD 16 is disposed at the base of the observation system 12*a*. Also, an illumination optical system 13*a* is disposed from each of the illumination windows 13 toward the base side. An LED 17 is disposed at the base end of each illumination optical system 13*a*. The signal transmission cable extending form the CCD 16 and the power source cable extending from the LEDs 17 are each connected to the connecting terminals 31 of the connector portion 30*a*. On the other hand, multiple, two in the case, contact pins 32 are provided on the tip 5*a* of the insertion portion 2. The contact pins 32 are electrically connected to the two contact terminals 31 of the camera unit 30. The contact pins 32 protrude from the inner circumferential face of the camera unit storage portion 5A by a predetermined amount. Connected to each of the contact pins 32 are the other ends of electric cables 11*a* of which the one ends are connected to contact terminals 4A.

Also, an O-ring 34 is provided on the opening side of the camera unit storage portion 5A. The O-ring 34 is provided in close contact with the outer circumferential face of the connector portion 30*a* of the camera unit 30. Water-tightness between the connecter portion 30*a* and the camera unit storage portion 5A is maintained by this O-ring 34.

Due to the above, the camera unit 30 can be easily attached and detached to and form the insertion portion 2 via the fixing member 33. Accordingly, the camera unit 30 can be easily replaced, and also the CCD 16 and LEDs 17 built into the camera unit 30 can be easily maintained.

A second embodiment of the present invention will be described with reference to FIGS. 14 through 16.

Note that in describing the second embodiment, members with the same configuration and same operations as those of the endoscope system according to the first embodiment will be denoted with the same reference numerals and description thereof will be omitted.

Figure 14:
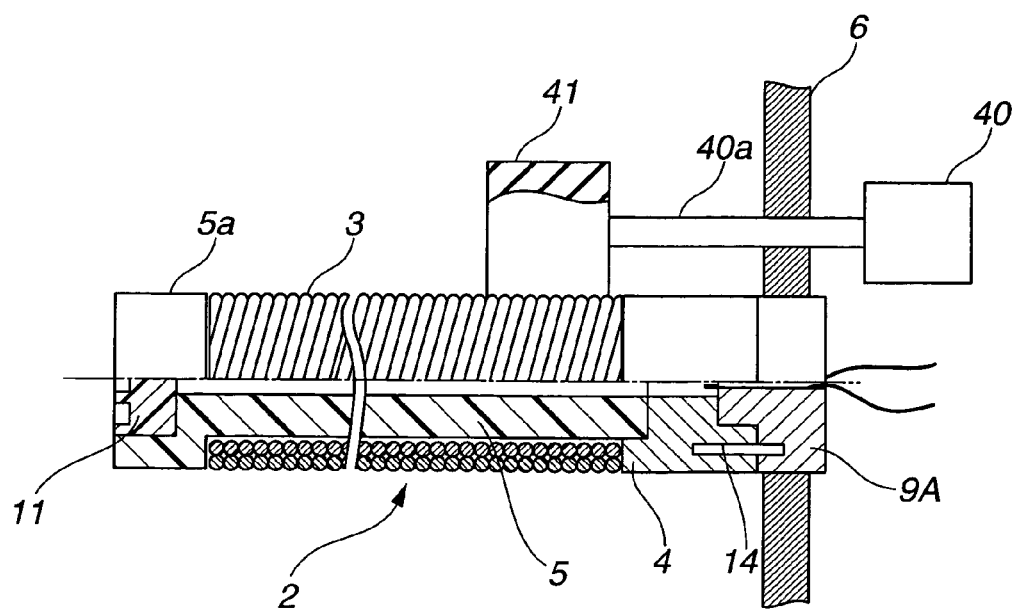
FIG. 14 is a longitudinal partial cross sectional view describing the insertion portion and the insertion portion rotating device in a second embodiment.

As shown in FIG. 14, the guide tube 3 according to the present embodiment is fit to the outer circumference portion of the insertion portion body 5 in a movable manner, between the tip 5*a* of the insertion portion and the connector portion 4. That is to say, while the guide tube 3 according to the first embodiment was integrally disposed to the insertion portion body 5, with the present embodiment the guide tube 3 is disposed to the insertion portion body 5 so as to be rotatable on the longitudinal axis thereof. Note that with the present embodiment, surface processing with high lubricity, such as fluorine coating, may be applied to the inner circumferential face of the guide tube 3 to reduce resistance upon rotating.

With the rotating device 6 according to the present embodiment as well, a motor 40 is internally provided. A motor shaft 40*a* of the motor 40 externally protrudes from a side plate portion of the rotating device 6. The motor shaft 40*a* is parallel to an insertion portion holding section 9A. A generally-cylindrical rotating member 41 formed of an elastic material is disposed on the tip portion of the motor shaft 40*a*. The rotating member 41 is disposed so as to be in tight contact with the outer circumferential face of the base portion of the guide tube 3 with a predetermined pressing force. Accordingly, driving the motor 40 rotates the rotating member 41 disposed in close contact with the guide tube 3, and the guide tube 3 is rotated in a predetermined direction on the longitudinal axis as to the insertion portion body 5. In the present embodiment, the insertion portion holding section 9A is integrally fixed to the side plate portion of the rotating device 6. Accordingly, there is no need to provide a collector such as a slip ring 18 to the rotating device 6, thereby simplifying the configuration of the rotating device 6.

Due to the above, at the time of inserting the insertion portion 2 with the guide tube 3 in a rotating state into a body cavity such as the large intestine, only the guide tube 3 is rotated on the longitudinal axis. That is to say, the insertion portion body 5 making up the insertion portion 2 does not rotate. Accordingly, the camera unit 11 fit to the tip 5*a* also does not rotate. Thus, rotating of images captured by the camera unit 11 of the tip 5*a* can be prevented. Accordingly, image processing for handling rotations of the tip 5*a* at the video processor 7 is unnecessary.

Accordingly, observations signals output from the CCD 16 of the camera unit 11 are continuously generated into video signals by the vide processor 7, and displayed on the monitor 8 screen. Also, there is no need to have the optical axis of the observation window 12 provided to the camera unit 11 disposed on the rotation axis of the insertion portion 2, and thus the disposing position of the observation window 12 and illumination windows 13 of the camera unit 11 can be freely changed, and the degree of freedom of design is improved. Accordingly, disposing the illumination windows 13 and the observation window 12 such that light distribution balance within the image capturing range is optimal, or disposing the illumination windows 13 and the observation window 12 to minimize the diameter of the tip portion, and so forth, can be performed as suitable.

Figure 15:
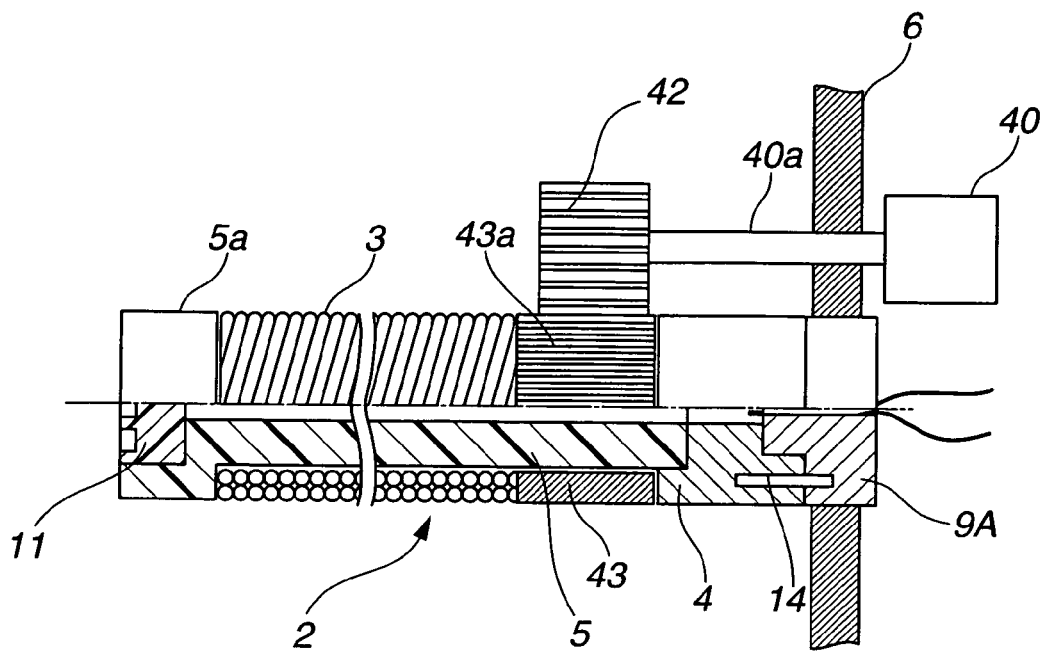
FIG. 15 is a longitudinal partial cross sectional view describing the insertion portion and the insertion portion rotating device in a modification of the second embodiment.

Note that a configuration may be made wherein, instead of having the rotating member 41 in close contact with the outer circumferential face of the base portion of the guide tube 3, an annular gear 43 is integrally provided to the base end portion of the guide tube 3, as shown in FIG. 15.

Formed on the gear 43 are, for example, spur-like gear grooves 43a, a cylindrical gear 42 is provided at the tip portion of the motor shaft 40a of the motor 40. The cylindrical gear 42 provided to the motor shaft 40a of the motor 40 meshes with the gear grooves 43a of the gear 43 provided to the guide tube 3. Accordingly, driving the motor 40 rotates the cylindrical gear 42, and the rotations of the cylindrical gear 42 are transmitted to the gear 43 on which are formed the gear grooves 43a, so that only the guide tube 3 rotates in the predetermined direction on the longitudinal axis.

Note that the rotation direction of the guide tube 3 shown in FIGS. 14 and 15 is the counter-clockwise direction on the longitudinal axis of the guide tube 3, likely with the first embodiment. Thus, contact of the guide tube 3 with the walls of the large intestine is increased, and insertability of the insertion portion 2 to the large intestine improves.

Figure 16:
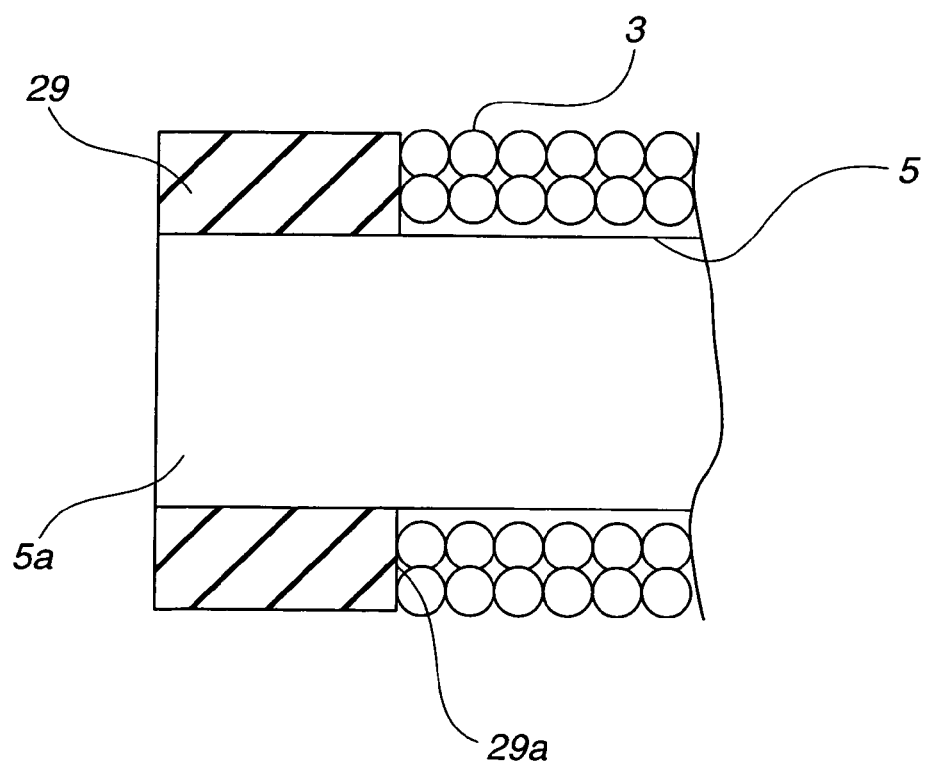
FIG. 16 is a cross sectional view describing a stopper member which is placed on the tip of the insertion portion.

Note that as shown in FIG. 16, the external diameter of the tip 5a of the insertion portion 2 is formed to be the same diameter as with the insertion portion body 5. An abutting member 29a for preventing falling out of the guide tube 3 is fixedly provided to the tip 5a. Thus, the tip portion of the guide tube 3 abuts against the abutting portion 29a, and the same configuration as that described above can be obtained. The stopper member 29 is formed of an elastic member fixed in close contact to the outer circumferential face of the tip 5a of the insertion portion 2, or a rigid member screwed to the outer circumferential face of the tip 5a. A male screw is formed on the outer circumferential face of the tip 5a, and a female screw is formed on the inner hole of the stopper member 29.

According to this configuration, the guide tube 3 can be removed from the insertion portion body 5 which makes up the insertion portion 2, by removing the stopper member 29 from the tip 5a. Accordingly, the staff can perform washing and sterilization with high reliability with ease, since the insertion portion body 5 and the guide tube 3 are in a separated state. Note however that the stopper member 29 and the guide tube 3 may be disposable.

Also, the rotation direction of the guide tube 3 described above is the counter-clockwise direction on the longitudinal axis of the guide tube 3, likely with the first embodiment. Thus, contact of the guide tube 3 with the walls of the large intestine is increased, and insertability of the insertion portion to the large intestine improves.

A third embodiment of the present invention will be described with reference to FIGS. 17 through 20.

With this embodiment as well, members with the same configuration and same operations as those of the endoscope system according to the first embodiment and second embodiment will be denoted with the same reference numerals and description thereof will be omitted.

Figure 17:
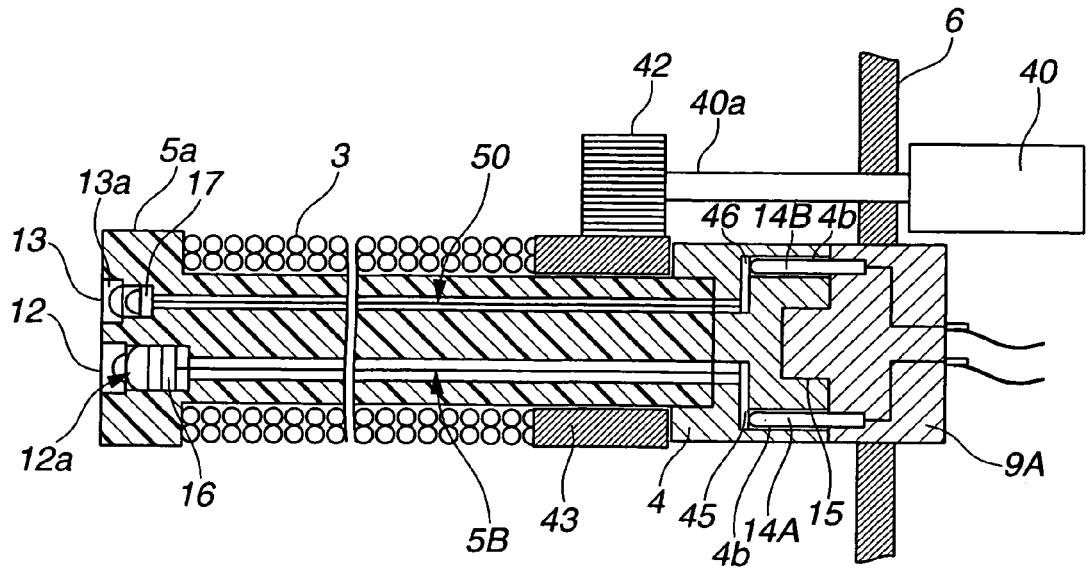
FIG. 17 is a longitudinal partial cross sectional view describing the insertion portion and an insertion portion rotating device in a third embodiment.

As shown in FIG. 17, an observation window 12 and illumination window 13 are provided to the distal face of the tip 5a of the insertion portion 2. Provided within the tip 5a are an observation optical system 12a having a CCD 16, and two illumination optical systems 13a having LEDs 17. A CCD wiring through hole 5B and an LED wiring through hole 5C are provided within the connector portion 4 of the insertion portion body 5. A signal transmission cable extending from the CCD 16 is inserted through the CCD wiring through hole 5B, and a power source cable extending from the LEDs 17 is inserted through the wiring through hole 5C.

A CCD connection terminal 45 is provided at the end of the CCD wiring through hole 5B of the connector portion 4. The signal transmission cable is connected to the CCD connection terminal 45. On the other hand, an LED connection terminal 46 is provided to the end of the LED wiring through hole 5C. The power cable is connected to the LED contact terminal 46. These CCD connection terminal 45 and Led connection terminal 46 are provided such that each is exposed from the hole bases of the two pin holes 4b of the connector portion 4.

At the time of linking the insertion portion 2 to the insertion portion holding section 9, the two pins 14A and 14B provided to the insertion portion holding section 9A are respectively inserted into the tow pin holes 4b provided to the connector portion 4. In the linked state, the pin 14A comes into contact with the CCD contact terminal 45, and the pin 14B comes into contact with the LED contact terminal 46. The signal transmission cable is connected to the pin 14A. Accordingly, the pin 14A is a pin terminal for transmitting the observation signals output from the CCD 16 to the video processor 7. On the other hand, the power source cable is connected to the pin 14B. Accordingly, the pin 14B is a pin terminal for supplying LED power source to the LEDs 17.

The configuration of the linking portion between the connector portion 4 of the insertion portion 2 and the insertion portion holding section 9A of the rotating device 6, will be described in detail, with reference to FIGS. 18 through 20.

Figure 18:
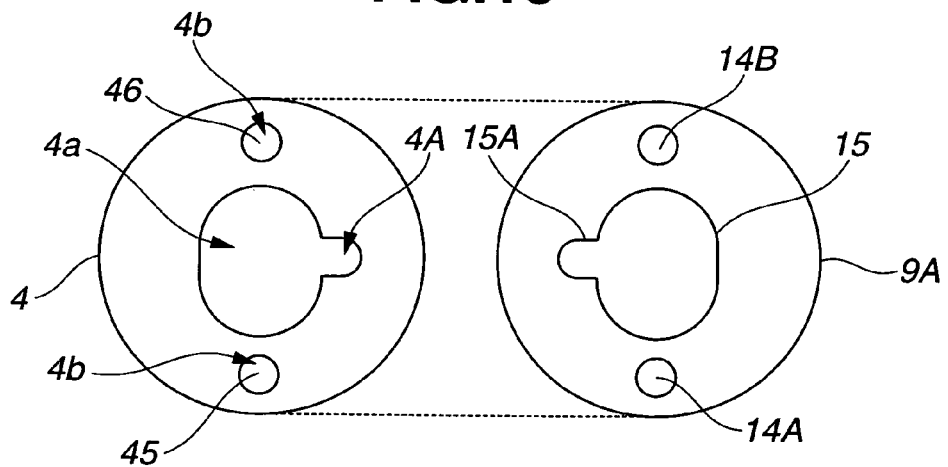
FIG. 18 is a diagram describing a configuration example of the coupling part which prevents the misconnection between the connector part of the endoscope insertion portion and the insertion portion holding section in the insertion portion rotating device.

A key portion 15A protruding toward the outer circumference side is provided on a protrusion 15 making up the insertion portion holding section 9A provided to the rotating device 6, as shown in FIG. 18. Corresponding to this, a keyhole portion 4A is provided to a fitting hole 4a provided to the connector portion 4 of the insertion portion 2. The keyhole portion 4A is configured such that the key portion 15A provided to the protrusion 15 of the insertion portion holding section 9A is retained therein. Accordingly, the connector portion 4 of the insertion portion 2 and the insertion portion holding section 9A of the rotating device 6 are linked at a predetermined position relation set beforehand, at the time of linking. Accordingly, the key portion 15A and the keyhole portion 4A are positioning members, such that in a state of linking, the pin 14A and the CCD contact terminal 45 are brought into contact in a sure manner, and the pin 14B and the LED contact terminal 46 are brought into contact in a sure manner.

Figure 19:
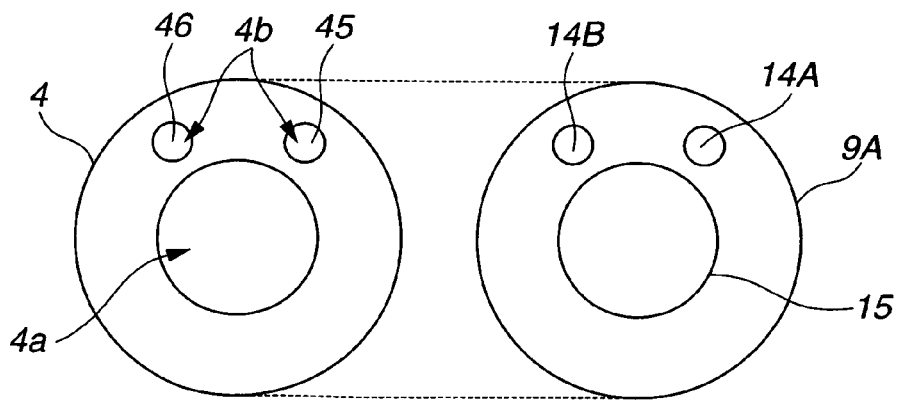
FIG. 19 is a diagram describing another configuration example of the coupling part which prevents the misconnection between the connector part of the endoscope insertion portion and the insertion portion holding section in the insertion portion rotating device.

Note that an arrangement may be made wherein, instead of providing positioning members such as the key portion 15A and keyhole portion 4A, the pins 14A and 14B also serve as positioning members, as shown in FIG. 19. Specifically, the pins 14A and 14B are disposed in non-point-symmetry as to the perimeter of the protrusion 16 of the insertion portion holding section 9A. At this time, the positions of the two pin holes 4B provided to the connector portion 4 of the insertion portion 2 are provided facing the pins 14A and 14B, and also the pin 14A is disposed so as to come into contact with the CCD contact terminal 45 and the pin 14B is disposed so as to come into contact with the LED contact terminal 46.

Figure 20:
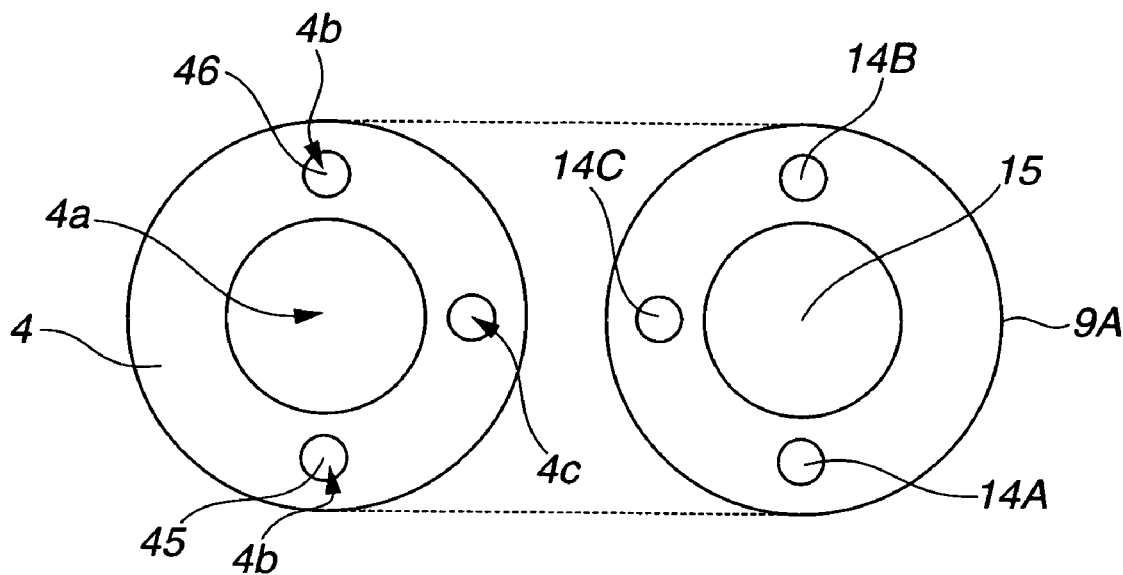
FIG. 20 is a diagram describing yet another configuration example of the coupling part which prevents the misconnection between the connector part of the endoscope insertion portion and the insertion portion holding section in the insertion portion rotating device.

Also, a positioning pin 14C may be provided separately from the pins 14A and 14B to the insertion portion holding section 9A, as shown in FIG. 20. At this time, a position hole 4c is provided to the connector portion 4 of the insertion portion 2 to which the positioning pin 14C provided to the insertion portion holding section 9A is inserted.

According to the above, the connector portion 4 of the insertion portion 2 and the insertion portion holding section 9A of the rotating device 6 are always linked only by a predetermined positional relation. That is to say, at the time of linking, the pin 14A of the insertion portion holding section 9A is inserted in the pin hole 4b of the CCD contact terminal 45 side in a sure manner, and the pin 14B is inserted into the pin hole 4b of the LED contact terminal 46 side in a sure manner. Accordingly, the staff can perform linking connection of the connector portion 4 of the insertion portion 2 and the insertion portion holding section 9A of the rotating device 6 without taking into consideration the orientation thereof.

Note that with the endoscope system 1 wherein the insertion portion 2 rotates, rotation marks may occur on the insertion portion 2 depending on the position of the pins 14A and 14B. Accordingly, with the endoscope system 1 wherein the insertion portion 2 rotates, the positions of protrusion of the pins 14A and 14B of the rotating device 6 are preferably in point symmetry to the center of the insertion portion holding section 9A, as shown in FIG. 18.

According to the above, in addition to the operations and advantages of the first and second embodiments, with the present embodiment the power source cable connected to the LED 17 and the signal transmission cable connected to the CCD 16 are each passed through respective through holes 5B and 5C within the insertion portion body 5. Accordingly, electrical trouble occurring due to the power source cable and signal transmission cable being in close proximity can be avoided. Specifically, noise is prevented from entering the observation signals output from the CCD 16, and consequently, a good endoscope image is displayed on the screen of the monitor 8. Also, the connector portion 4 of the insertion portion 2 and the insertion portion holding section 9A of the rotating device 6 are linked only in a predetermined fitting direction, so the pin 14A of the insertion portion holding section 9A is inserted in the pin hole 4b of the CCD contact terminal 45 side in a sure manner, and the pin 14B is inserted into the pin hole 4b of the LED contact terminal 46 side in a sure manner. Accordingly, connection mistakes wherein the connector portion 4 of the insertion portion 2 and the insertion portion holding section 9A of the rotating device 6 are erroneously connected are resolved, thereby reducing the load on the staff.

A fourth embodiment of the present invention will be described with reference to FIGS. 21 through 24.

With this embodiment as well, members with the same configuration and same operations as those of the endoscope system according to the first embodiment through third embodiment will be denoted with the same reference numerals and description thereof will be omitted.

Figure 21:
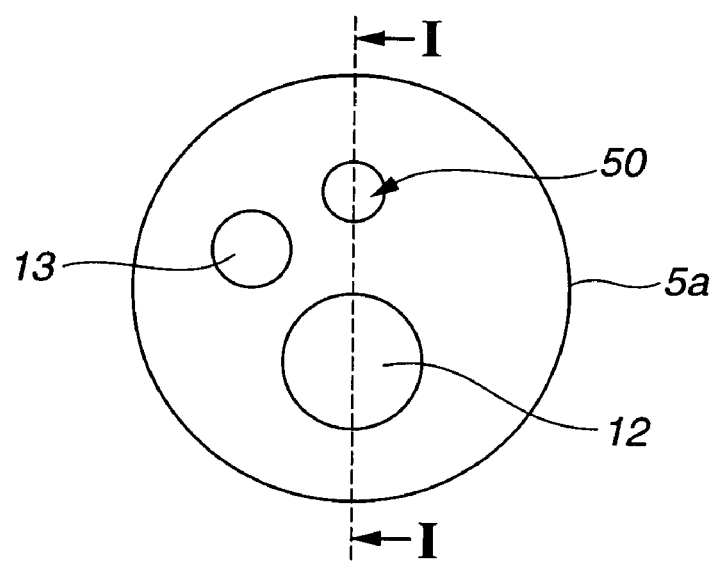
FIG. 21 is a front view illustrating the tip of the insertion portion in a fourth embodiment.
Figure 22:
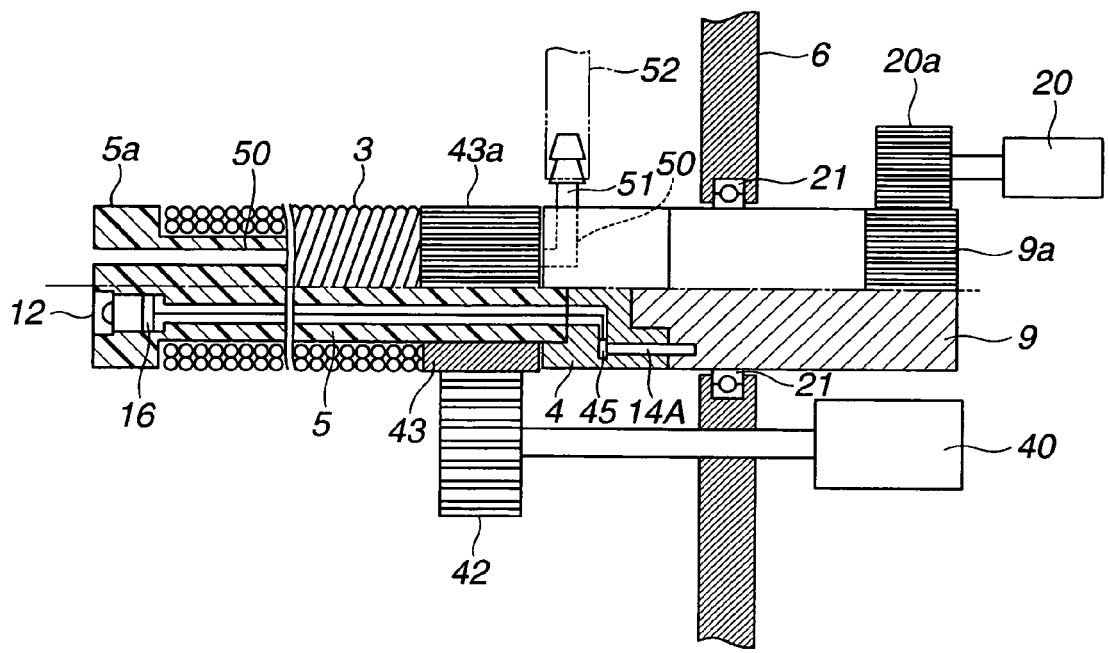
FIG. 22 is a longitudinal partial cross sectional view describing the insertion portion and the insertion portion rotating device in the fourth embodiment.

As shown in FIG. 21, an opening of a channel 50 is provided to the tip face of the tip 5a of the insertion portion 2 with the present embodiment. As shown in FIG. 22, the channel 50 is a through hole extending to the connector portion 4 of the insertion portion 2. The opening end of the channel 50 at the connector portion 4 side of the insertion portion 2 is provided on the side circumferential face of the connector portion 4, for example. A tube connector 51 is provided to the opening of the connector portion 4 side, and one end of the tube 52 is detachably linked to the tube connector 51. The other end of the tube 52 is selectively connected to an external device, e.g., an air/water pump, suction pump, syringe, or the like, which are selected as appropriate according to the various usages thereof.

Gear grooves 9a are provided to the base portion of the insertion portion holding section 9 of the rotating device 6, in the same way as with the first embodiment. The cylindrical gear 20a provided to the top portion of the motor shaft of the motor 20 meshes with the gear grooves 9a. With the present embodiment, the insertion portion holding section 9 is rotated in the counter-clockwise direction and clockwise direction on the longitudinal axis by the motor 20. Accordingly, the insertion portion 2 is also turned in the counter-clockwise direction and the clockwise direction on the longitudinal axis. The turning range of the insertion portion holding section 9 is restricted to a predetermined range, e.g., 360°. Restriction of the turning of the insertion portion holding section 9 is performed by controlling the turning of the motor 20, based on control signals output from the control unit 22a of the control device 22.

Note that with the present embodiment, the guide tube 3 is rotated in the counter-clockwise direction on the longitudinal axis as to the insertion portion body 5 making up the insertion portion 2 by the motor 40. Also, rotation of the insertion portion 2 is not restricted to turning on longitudinal axis by the motor 20, and is suitable as long as the connector portion 4 of the insertion portion 2 is provided with rotation on the longitudinal axis. Also, an arrangement may be made wherein the rotating device 6 is provided with a so-called rack-and-pinion, to realize reciprocal movement of the insertion portion 2 in the longitudinal direction, for example.

Accordingly, feeding air or water, or performing suction, to or from the large intestine or other body cavities, is enabled by providing the channel 50 to the insertion portion 2. Also, turning the insertion portion 2 within a predetermined turning range by the motor 20 allows the staff to change the position of the channel 50 and the observation window 12 to a desired position. These improve the efficiency of endoscopy, diagnosis, and so forth.

Figure 23:
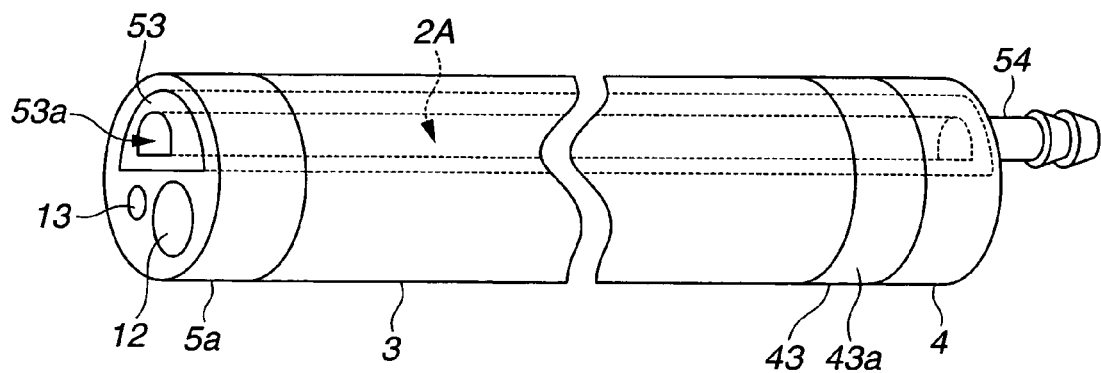
FIG. 23 is an external view of an insertion portion into which a replacement unit is inserted.

Note that, as shown in FIG. 23, a replacement unit 53 may be provided to the insertion portion 2 which is detachable from the tip 5a to the connector portion 4. In more detail, a through hole 2A of generally the same shape as the outer shaft of the replacement unit 53 is provided in the longitudinal direction from the tip 5a of the insertion portion 2 up to the connector portion 4. Accordingly, a replacement unit 53 can be detachably inserted into the through hole 2A of the insertion portion 2. The replacement unit 53 is a tubular member having flexibility, and has a channel 53a. A tube connector 54 linking to the channel 53a is provided on the base portion of the replacement unit 53. A biocompatible lubricant such as grease or a powder or the like, for example is applied to the outer face of the replacement unit 53. Accordingly, the staff can readily insert the replacement unit 53 into the through hole 2A of the insertion portion 2. As with the above embodiment, the tube connector 54 is selectively connected to an external device, e.g., an air/water pump, suction pump, syringe, or the like, as appropriate according to the various usages thereof.

Figure 24:
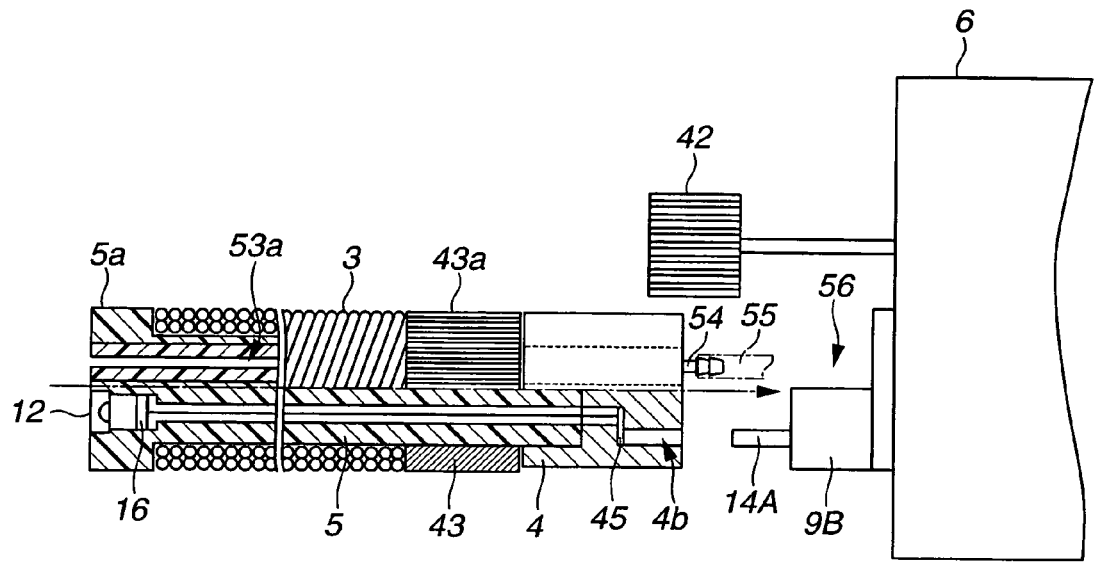
FIG. 24 is a longitudinal partial cross sectional view describing an insertion portion in which a replacement unit is disposed.

As shown in FIG. 24, a notch 56 is provided to the insertion portion holding section 9B of the rotating device 6 to which is linked the insertion portion 2 having the through hole 2A where the replacement unit 53 is disposed. Accordingly, at the time of linking the connector portion 4 of the insertion portion 2 with the replacement unit 53 disposed in the insertion hole 2A, to the insertion portion holding section 9B of the rotating device 6, the tube connector 54 and the tube 55 linked to the tube connector 54 are prevented from coming into contact with the insertion portion holding section 9B.

Also, the insertion portion 2 may be turned on the longitudinal axis by the insertion portion holding section 9B of the rotating device 6. Further, a washing nozzle or a water feed nozzle or the like may be provided to the tip face of the replacement unit 53 to wash the observation window 12 via the channel 50. Moreover, the number of channels 53a provided to the replacement unit 53 is not restricted to one, and may be plural.

Due to the above, the staff can replace various types of replacement units 53 to be inserted to the insertion portion 2, thereby performing various types of endoscopy and diagnosis and the like.

Further, the configuration shown in the following FIGS. 25 through 29 may be provided to the above-described endoscope system 1 according to the first embodiment through fourth embodiment.

Figure 25:
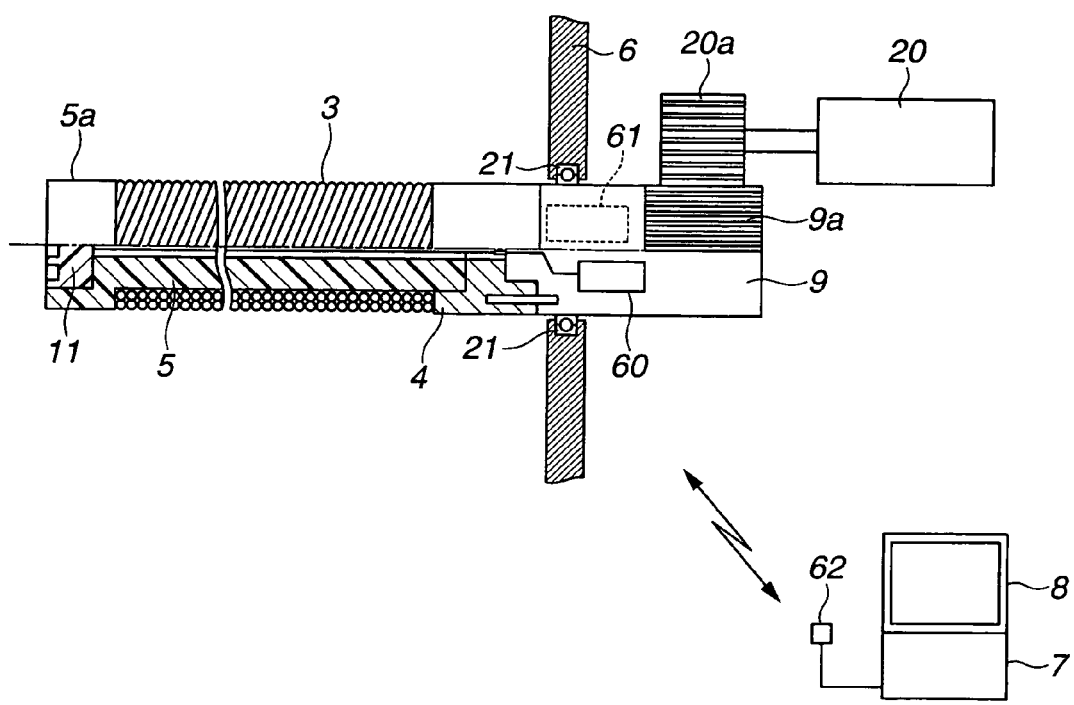
FIG. 25 is a diagram describing a radio transmitter and a power battery which are installed at the insertion portion holding section in the insertion portion rotating device.

With the rotating device 6 according to the endoscope system 1 shown in FIG. 25, a wireless transmitter 60 and a power source battery 61 are provided within the insertion portion holding section 9. The power source battery 61 supplies driving power to the CCD 16, LEDs 17, and wireless transmitter 60. Note that the battery 61 may be either a chargeable battery or a disposable type.

The wireless transmitter 60 wirelessly transmits observation signals output and transmitted from the CCD 16 in the insertion portion 2 to a receiver 62. The receiver 62 is connected to the video processor 7 by a cable or the like. The observation signals received at the receiver 62 are supplied to the video processor 7. Accordingly, the video signals generated at the video processor 7 are output to the monitor 8, and an endoscope image image-captured by the CCD 16 is displayed on the monitor 8 screen. Note that the receiver 62 may be built into the video processor 7.

Due to the above, the power source cable and signal transmission cable extended from the insertion portion holding section 9 of the rotating device 6 for rotating the insertion portion 2 to the control device 22 and the like can be eliminated, and also signals can be exchanged without complex parts such as the slip ring 18 or the like. Accordingly, the configuration of the rotating device 6 can be simplified, thereby realizing reduction in size of the device.

Figure 26:
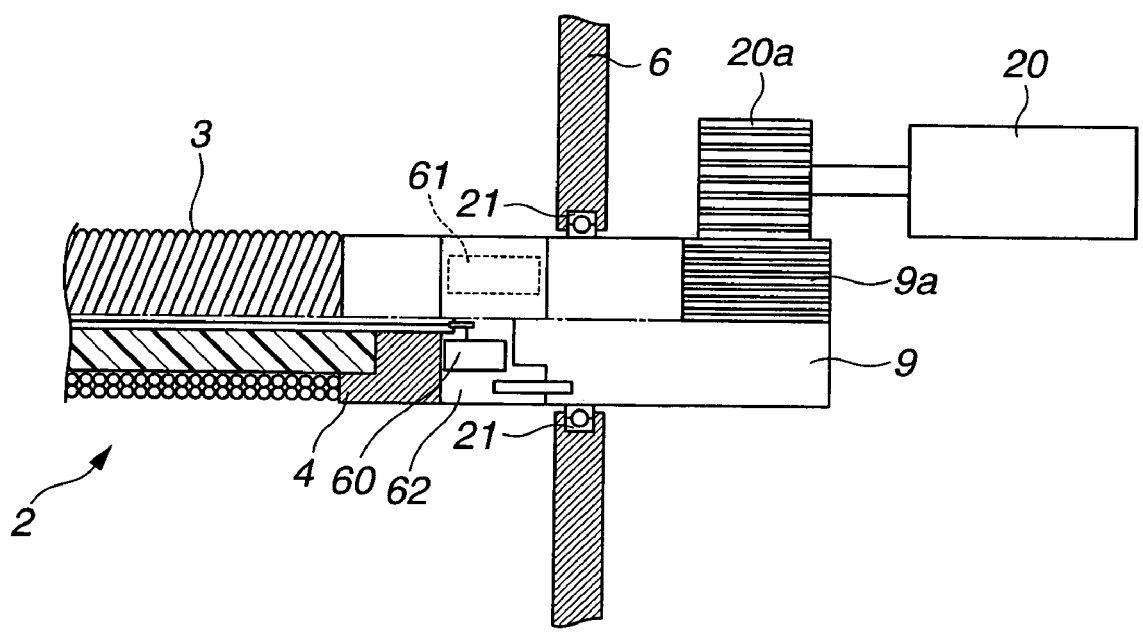
FIG. 26 is a diagram describing a connector unit part which is installed at the connector part of the insertion portion.

The endoscope system 1 shown in FIG. 26 is a configuration wherein a connector unit 62 has been built onto the base side of the connector portion 4 of the insertion portion 2. Provided in the connector unit 62 are the wireless transmitter 60 and power source battery 61. The connector unit 62 is detachably mounted to the insertion portion holding section 9 of the rotating device 6. The connector unit 62 may also be detachably mounted to the connector portion 4 of the insertion portion 2.

Thus, the connector unit portion 62 provided with the wireless transmitter 60 and power source battery 61 is detachable from the insertion portion holding section 9 and the connector portion 4, and therefore expensive equipment such as the wireless transmitter 60 and power source battery 61 can be reused. Thus, an inexpensive endoscope system 1 with reduced running costs can be realized.

Figure 27:
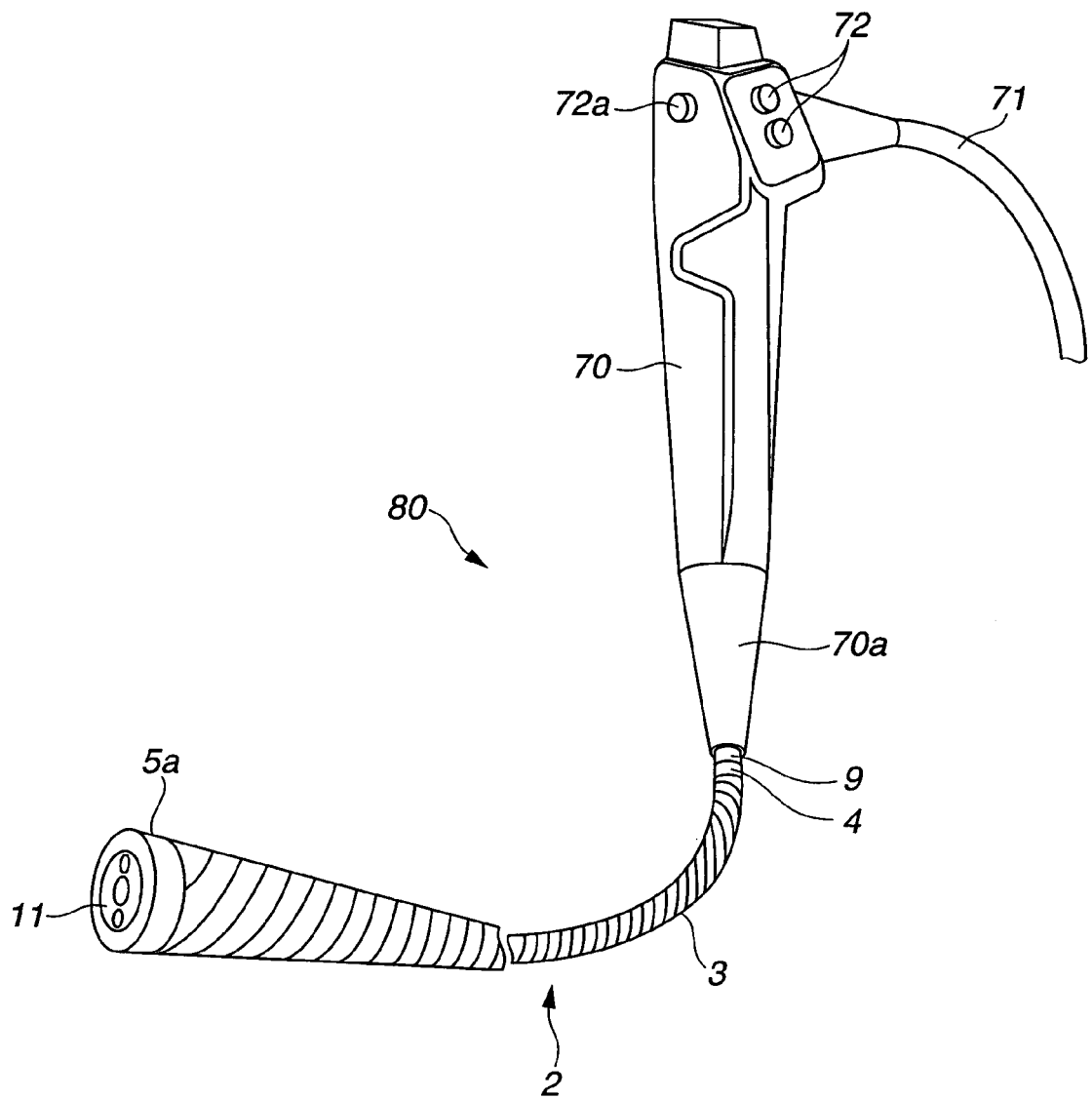
FIG. 27 is an external view illustrating the rotating device having the shape of an endoscope operation part and the insertion portion which is detachable from the rotating device.

An arrangement may be made such as shown in FIG. 27, wherein the external shape of the rotating device 6 is that of a rotating device 70 having an operating portion shape which can be grasped by the staff as with a conventional endoscope portion. Thus, linking the connector portion 4 of the insertion portion 2 to the insertion portion holding section 9 provided to the rotating device 70 configures an endoscope device 80. A universal cord 71 to be connected to various types of external equipment extends from, for example, the side portion of the rotating device 70. To one side face of the rotating device 70 in the proximity of the universal cord 71, two switches 72, and one stop switch 72a, for example, are provided. The two switches 72 are for rotating operations of the insertion portion 2 in the counter-clockwise direction and the clockwise direction, respectively, on the longitudinal axis. The stop switch 72a is for stopping turning of the insertion portion 2.

Figure 28:
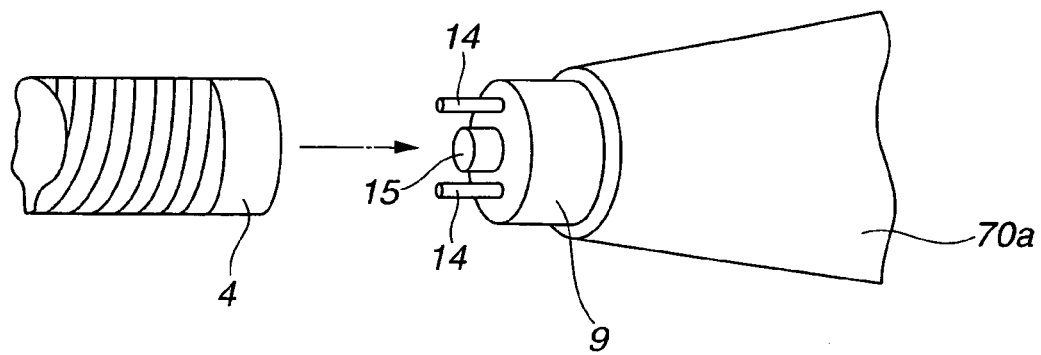
FIG. 28 is a diagram describing the detachment relation between the insertion portion and the insertion portion holding section.
Figure 29:
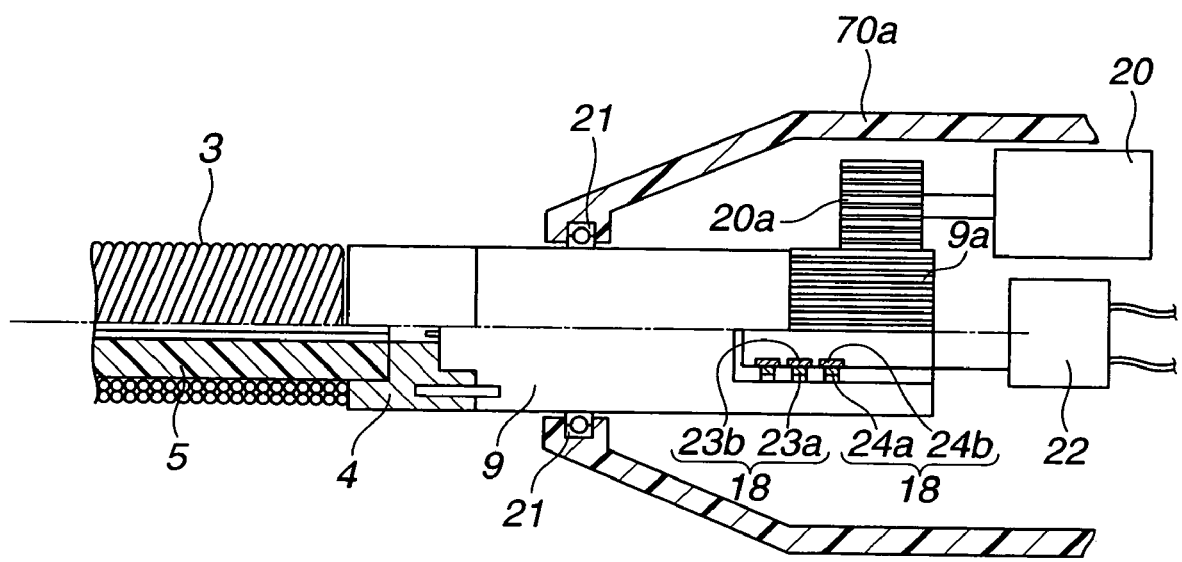
FIG. 29 is a view describing the insertion portion which is detachable from the rotating device having the shape of an operating part.

Also, the insertion portion holding section 9 protrudes from the tip opening of a buckling prevention portion 70a which is the tip portion of the turning device 70. Also, as shown in FIG. 28, the insertion portion holding section 9 and the connector portion 4 of the insertion portion 2, protruding from the buckling prevention portion 70a, are detachable. Further, as shown in FIG. 29, the insertion portion holding section 9 is held so as to turn on the longitudinal axis as to the rotating device 70. Specifically, the insertion portion holding section 9 is turnably held by a bearing 21. The bearing 21 is disposed on the inner circumferential face of the tip opening of the buckling prevention portion 70a of the rotating device 70. The gear grooves 9a are provided to the base portion of the insertion portion holding section 9. The cylindrical gear 20a provided to the motor shaft of the motor 20 meshes with the gear grooves 9a. Accordingly, driving the motor 20 by operating the switches 72 rotates the insertion portion holding section 9 in the predetermined direction on the longitudinal axis. A slip ring 18 is provided on the base side of the insertion portion holding section 9. A cable extending from the control device 22 is passed through the universal cord 71, via the rotating device 70.

Consequently, linking the insertion portion 2 to the rotating device 70 having the operating portion shape enables operability at the time of inserting the insertion portion 2 into a body cavity such as the large intestine or the like, while eliminating the sense of unfamiliarity with the staff using the endoscope system 1 since the shape is that of a conventional endoscope device.

Note that the present invention is not restricted to the above-described embodiments, and that various modifications can be made within the spirit and scope of the invention.

What is claimed is:

1. An insertion device comprises:
   a long-sized insertion portion to be inserted into a subject;
   a propulsion force generating portion provided on the outer peripheral face of the insertion portion and configured of a spiral-shaped portion that contacts an intestinal wall of the subject to generate a propulsion force for the insertion portion;
   a rotating portion for rotating the propulsion force generating portion on the longitudinal axis of the insertion portion;
   an image capturing device for observing an image of the subject, provided at the tip of the insertion portion so as to be rotatable according to the rotation of the propulsion force generating portion;
   a first electric contact which is connected electrically to the image capturing device and moves rotationally according to the rotation of the propulsion force generating portion provided on the insertion portion; and
   a second electric contact, on which the first electric contact which moves rotationally according to the rotation of the propulsion force generating portion, is provided slidably, and is connected electrically to the first electric contact.

2. The insertion device according to claim 1, further comprising:

an illumination light irradiating portion for irradiating illumination light onto the subject, provided at the tip of the insertion portion so as to be rotatable according to the rotation of the propulsion force generating portion:

a third electric contact which is electrically connected with the illumination light irradiating portion, and which rotationally moves according to the rotation of the propulsion force generating portion provided to the insertion portion; and a fourth electric contact, on which the third electric contact which moves rotationally according to the rotation of the propulsion force generating portion is provided slidably, and is connected electrically to the third electric contact.

3. The insertion device according to claim 2, wherein the third electric contact and the fourth electric contact make up a slip ring.

4. The insertion device according to claim 3, wherein the third electric contact is a brush portion, and the fourth electrical contact is a ring portion.

5. The insertion device according to claim 1, wherein the first electric contact and the second electric contact make up a slip ring.

6. The insertion device according to claim 5, wherein the first electric contact is a brush portion, and the second electrical contact is a ring portion.

7. An endoscope device comprising:

a long-sized insertion portion to be inserted into a subject;

a propulsion force generating portion provided on the outer peripheral face of the insertion portion and configured of a spiral-shaped portion that contacts an intestinal wall of the subject to generate a propulsion force for the insertion portion;

a rotating portion for rotating the propulsion force generating portion on the longitudinal axis of the insertion portion;

an image capturing device for observing an image of the subject, provided at the tip of the insertion portion so as to be rotatable according to the rotation of the propulsion force generating portion;

wherein an insertion portion rotating device having the rotating portion is provided with a transmitter for externally transmitting observation signals output from an image capturing unit;

a first electric contact which is connected electrically to the image capturing device and moves rotationally according to the rotation of the propulsion force generating portion provided on the insertion portion; and a second electric contact, on which the first electric contact which moves rotationally according to the rotation of the propulsion force generating portion, is provided slidably, and is connected electrically to the first electric contact.

* * * * *

UNITED STATES PATENT AND TRADEMARK OFFICE
CERTIFICATE OF CORRECTION

| | |
|---|---|
| PATENT NO. | : 7,621,867 B2 |
| APPLICATION NO. | : 11/599578 |
| DATED | : November 24, 2009 |
| INVENTOR(S) | : Yasuhito Kura et al. |

Page 1 of 1

It is certified that error appears in the above-identified patent and that said Letters Patent is hereby corrected as shown below:

On the title page item (63) should read: Continuation of application No. PCT/JP2005/008913, filed on May 16, 2005

Signed and Sealed this

Sixteenth Day of March, 2010

David J. Kappos
*Director of the United States Patent and Trademark Office*